(12) United States Patent
Wasielewski

(10) Patent No.: US 8,470,308 B2
(45) Date of Patent: *Jun. 25, 2013

(54) ENHANCED MEDICAL IMPLANT COMPRISING DISRUPTED TOOTH PULP AND TOOTH PARTICLES

(76) Inventor: Ray C. Wasielewski, New Albany, OH (US)

( * ) Notice: Subject to any disclaimer, the term of this patent is extended or adjusted under 35 U.S.C. 154(b) by 89 days.

This patent is subject to a terminal disclaimer.

(21) Appl. No.: 12/655,633

(22) Filed: Jan. 4, 2010

(65) Prior Publication Data

US 2010/0172863 A1    Jul. 8, 2010

Related U.S. Application Data

(63) Continuation-in-part of application No. 12/348,280, filed on Jan. 3, 2009, now abandoned.

(51) Int. Cl.
*C12N 5/00* (2006.01)
*A01N 63/00* (2006.01)

(52) U.S. Cl.
USPC ........................................ 424/93.1; 435/325

(58) Field of Classification Search
None
See application file for complete search history.

(56) References Cited

U.S. PATENT DOCUMENTS

| | | | |
|---|---|---|---|
| 5,131,850 A | 7/1992 | Brockbank | |
| 5,424,207 A | 6/1995 | Carpenter et al. | |
| 5,855,619 A | 1/1999 | Caplan et al. | |
| 5,885,829 A | 3/1999 | Mooney et al. | |
| 6,174,333 B1 | 1/2001 | Kadiyala et al. | |
| 6,194,137 B1 | 2/2001 | Khirabadi et al. | |
| 6,280,925 B1 | 8/2001 | Brockbank | |
| 6,303,341 B1 | 10/2001 | Hiatt et al. | |
| 6,596,531 B2 | 7/2003 | Campbell et al. | |
| 6,673,594 B1 | 1/2004 | Owen et al. | |
| 6,740,484 B1 | 5/2004 | Khirabadi et al. | |
| 6,767,740 B2 | 7/2004 | Sramek et al. | |
| 6,890,968 B2* | 5/2005 | Angeletakis et al. | 523/115 |
| 6,899,915 B2 | 5/2005 | Yelick et al. | |
| 7,052,907 B2 | 5/2006 | Shi et al. | |
| 7,157,222 B2 | 1/2007 | Khirabadi et al. | |
| 7,270,946 B2 | 9/2007 | Brockbank et al. | |
| 7,282,222 B2 | 10/2007 | Phillips | |
| 7,497,686 B2 | 3/2009 | Sharpe et al. | |
| 7,563,459 B2 | 7/2009 | Phillips | |
| 7,588,936 B2 | 9/2009 | Sharpe | |
| 7,955,850 B2 | 6/2011 | Carinci et al. | |
| 8,048,443 B2 | 11/2011 | Benedict et al. | |
| 8,048,999 B2 | 11/2011 | Yamanaka et al. | |
| 8,058,065 B2 | 11/2011 | Yamanaka et al. | |
| 2002/0119180 A1 | 8/2002 | Yelick et al. | |
| 2002/0159958 A1 | 10/2002 | Hiatt et al. | |
| 2003/0032693 A1* | 2/2003 | Angeletakis et al. | 523/116 |
| 2003/0068305 A1 | 4/2003 | Sramek et al. | |
| 2004/0018607 A1 | 1/2004 | Callen et al. | |
| 2004/0058442 A1 | 3/2004 | Shi et al. | |
| 2004/0121301 A1 | 6/2004 | Kato et al. | |
| 2005/0014256 A1 | 1/2005 | Sramek | |
| 2005/0106724 A1 | 5/2005 | Schierholz et al. | |
| 2005/0158535 A1 | 7/2005 | Zhang et al. | |
| 2006/0057542 A1 | 3/2006 | Sharpe et al. | |
| 2006/0122696 A1 | 6/2006 | Zhang et al. | |
| 2006/0228464 A1 | 10/2006 | Larson et al. | |
| 2006/0252151 A1 | 11/2006 | Sramek | |
| 2007/0009492 A1 | 1/2007 | Shi et al. | |
| 2007/0031859 A1 | 2/2007 | Yan et al. | |
| 2007/0087959 A1 | 4/2007 | Sfeir et al. | |
| 2007/0135335 A1 | 6/2007 | Collier et al. | |
| 2007/0190518 A1 | 8/2007 | Bourgeois et al. | |
| 2007/0196791 A1 | 8/2007 | Sramek et al. | |
| 2007/0238675 A1 | 10/2007 | Phillips et al. | |
| 2007/0258957 A1 | 11/2007 | Bowermaster et al. | |
| 2007/0274958 A1 | 11/2007 | Shi et al. | |
| 2007/0274960 A1 | 11/2007 | Harman et al. | |
| 2007/0286856 A1 | 12/2007 | Brown et al. | |
| 2008/0115244 A1 | 5/2008 | Hiatt et al. | |
| 2008/0124706 A1 | 5/2008 | Aoyama et al. | |
| 2008/0171951 A1 | 7/2008 | Fell | |
| 2008/0176325 A1 | 7/2008 | Bowermaster et al. | |
| 2008/0241206 A1 | 10/2008 | Constantz | |

(Continued)

FOREIGN PATENT DOCUMENTS

| | | |
|---|---|---|
| AU | 2006200478 B2 | 2/2006 |
| WO | WO 2006/010600 | 2/2006 |
| WO | WO 2007 030616 | 3/2007 |
| WO | PCT/US2010/00007 | 1/2010 |
| WO | WO 2010/078533 | 7/2010 |

OTHER PUBLICATIONS

Kasugai et al., Characterization of a system of mineralized-tissue formation by rat dental pulp cells in culture, Arch Oral Biol. 38(9):769-77, 1993.*
Abukawa, H. DDS, PhD et al., Reconstructing Mandibular Defects Using Autologous Tissue-Engineered Tooth and Bone Constructs, J Oral Maxillofac Surg 67 (2009): 335-347.
Author unknown, Application of Cryoconservation in human dental transplants, PLANER plc, book unknown, date unknown, 11 pgs.
Cheng, P.H. et al., Postnatal stem/progenitor cells derived from the dental pulp of adult chimpanzee, PubMed Abstract from BMC Cell Biol 9:20 (2008): 1 pg.

(Continued)

*Primary Examiner* — Deborah Crouch
(74) *Attorney, Agent, or Firm* — Wood, Herron & Evans, LLP

(57) ABSTRACT

A medical implant comprising in components from a tooth and stem cells harvested from at least one tooth. Tooth stem cells may be harvested from the dental pulp of mammalian teeth, such as unerupted third molars in humans. After the stem cells are removed and isolated from the other teeth tissue, the hard tooth may be ground into a base material for the manufacture of a porous matrix into which the tooth stem cells can be added. Additionally, soft tissue from the harvested tooth may be used as a carrier scaffold for soft tissue applications such as meniscal or cartilage repair.

11 Claims, 14 Drawing Sheets

U.S. PATENT DOCUMENTS

| | | |
|---|---|---|
| 2008/0306158 A1 | 12/2008 | Jewett et al. |
| 2008/0311093 A1 | 12/2008 | Skinner |
| 2009/0022693 A1 | 1/2009 | Thie et al. |
| 2009/0029322 A1 | 1/2009 | Duailibi et al. |
| 2009/0035282 A1 | 2/2009 | Schierholz et al. |
| 2009/0035376 A1 | 2/2009 | Carinci et al. |
| 2009/0105117 A1 | 4/2009 | Marx et al. |
| 2009/0110637 A1 | 4/2009 | Marx et al. |
| 2009/0130753 A1 | 5/2009 | Bowermaster et al. |
| 2009/0136988 A1 | 5/2009 | Reschiglian et al. |
| 2009/0148486 A1 | 6/2009 | Lu et al. |
| 2009/0155216 A1 | 6/2009 | Yamada et al. |
| 2009/0162326 A1 | 6/2009 | Siemonsmeier et al. |
| 2009/0274627 A1 | 11/2009 | Yamada et al. |
| 2009/0291065 A1 | 11/2009 | Laino et al. |
| 2009/0291496 A1 | 11/2009 | Racey et al. |
| 2009/0324555 A1 | 12/2009 | Thie et al. |
| 2010/0098670 A1 | 4/2010 | Yang |
| 2010/0104641 A1 | 4/2010 | Thie et al. |
| 2010/0105132 A1 | 4/2010 | Totey et al. |
| 2010/0136114 A1 | 6/2010 | Mao |
| 2010/0183563 A1 | 7/2010 | Kuboki et al. |
| 2010/0196854 A1 | 8/2010 | Shi et al. |
| 2010/0203481 A1 | 8/2010 | Murray et al. |
| 2010/0227396 A1 | 9/2010 | Lim et al. |
| 2010/0227399 A1 | 9/2010 | Funaki et al. |
| 2010/0285582 A1 | 11/2010 | Choung |
| 2011/0002895 A1 | 1/2011 | Ueda et al. |
| 2011/0003365 A1 | 1/2011 | Yamanaka et al. |
| 2011/0020310 A1 | 1/2011 | Nakashima et al. |
| 2011/0020930 A1 | 1/2011 | Wise et al. |
| 2011/0027332 A1 | 2/2011 | Benedict et al. |
| 2011/0039338 A1 | 2/2011 | Yamanaka et al. |
| 2011/0111499 A1 | 5/2011 | Torihashi et al. |
| 2011/0165098 A1 | 7/2011 | Jewett et al. |
| 2011/0177041 A1 | 7/2011 | Nakashima et al. |
| 2011/0177593 A1 | 7/2011 | Funaki et al. |
| 2011/0201110 A1 | 8/2011 | Tezuka et al. |
| 2011/0212523 A1 | 9/2011 | Kato et al. |
| 2011/0223668 A1 | 9/2011 | Gronthos et al. |
| 2011/0223669 A1 | 9/2011 | Yamanaka et al. |
| 2011/0250692 A1 | 10/2011 | Yamanaka et al. |
| 2011/0318830 A1 | 12/2011 | Briggs et al. |
| 2012/0027804 A1 | 2/2012 | Odermatt et al. |

OTHER PUBLICATIONS

Danilovic V. et al., Histological evaluation of platelet rich plasma and hydroxyapatite in apexogenesis: study on experimental animals, PubMed English Abstract from Vojnosanit Pregl 65:2 (2008): 1 pg.

Guest, D.J. et al., Equine embryonic stem-like cells and mesenchymal stromal cells have different survival rates and migration patterns following their injection into damaged superficial digital flexor tendon, Equine Vet J 42:7 (2010): 636-642.

Hough, S.R. et al., A continuum of cell states spans pluripotency and lineage commitment in human embryonic stem cells, PubMed Abstract from PLoS One 4:11 (2009): 7708.

Huang A.H. et al., Isolation and characterization of dental pulp stem cells from a supernumerary tooth, PubMed Abstract from J Oral Pathol Med 37:9 (2008): 571-574.

Huang, G.T.J. et al., Mesenchymal Stem Cells Derived from Dental Tissues vs. Those from Other Sources: Their Biology and Role in Regenerative Medicine, J Dent Res 88:9 (2009): 792-806.

Kurisaki A. et al., In vitro organogenesis using multipotent cells, Human Cell 23 (2010): 1-14.

Laino G. et al., A New Population of Human Adult Dental Pulp Stem Cells: A Useful Source of Living Autologous Fibrous Bone Tissue (LAB) J Bone Min Res 20:8 (2005): 1394-1402.

Laino G. et al., An Approachable Human Adult Stem Cell Source for Hard-Tissue Engineering, J Cell Phys 206 (2006): 693-701.

Office Action dated Dec. 15, 2010 in related U.S. Appl. No. 12/348,280.

Padilla F. et al., Relationships of trabecular bone structure with quantitative ultrasound parameters: In vitro study on human proximal femur using transmission and backscatter measurements, Bone 42 (2008): 1193-1202.

Reich P. DMD, Autogenous Transplantation of Maxillary and Mandibular Molars, J Oral Maxillofac Surg 66 (2008): 2314-2317.

Schwarts O., Cryopreservation of teeth before replantation or transplantation, PLANER plc, book unknown, Chapter 9, date unknown but prior to Mar. 8, 1995, 241-256.

Smith, A. Ph.D., Vitality of the Dentin-Pulp Complex in Health and Disease: Growth Factors as Key Mediators, J Dent Educ 67:6 (2003): 678-689.

Yao S. et al., Differentiation of Stem Cells in the Dental Follicle, Dept. of Comparative Biomedical Sciences, Louisiana State University, J Dent Res, SAGE journals online <http://jdr.sagepub.com/content/87/8/767.full#ref-13> Jan. 22, 2011, 7 pgs.

* cited by examiner

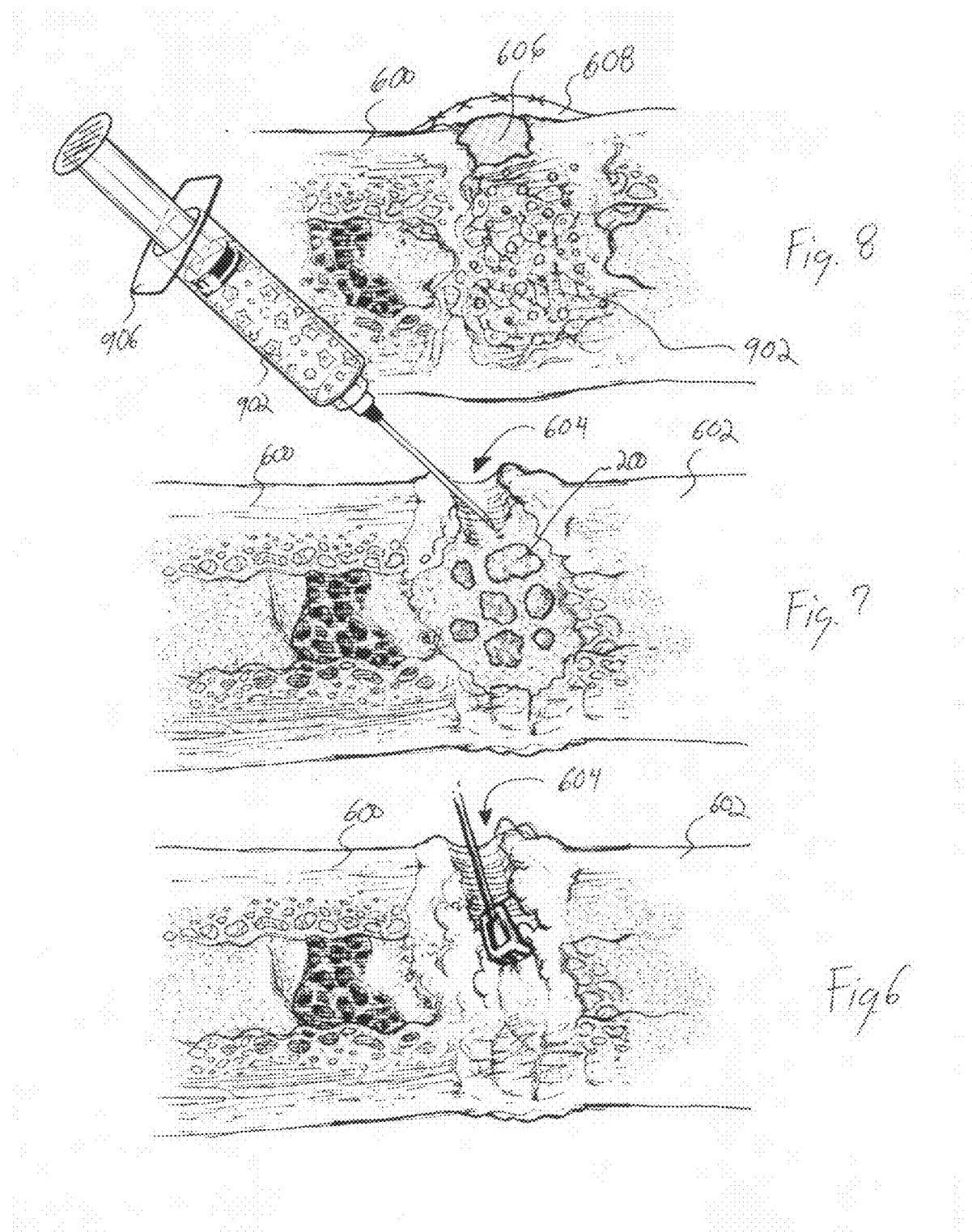

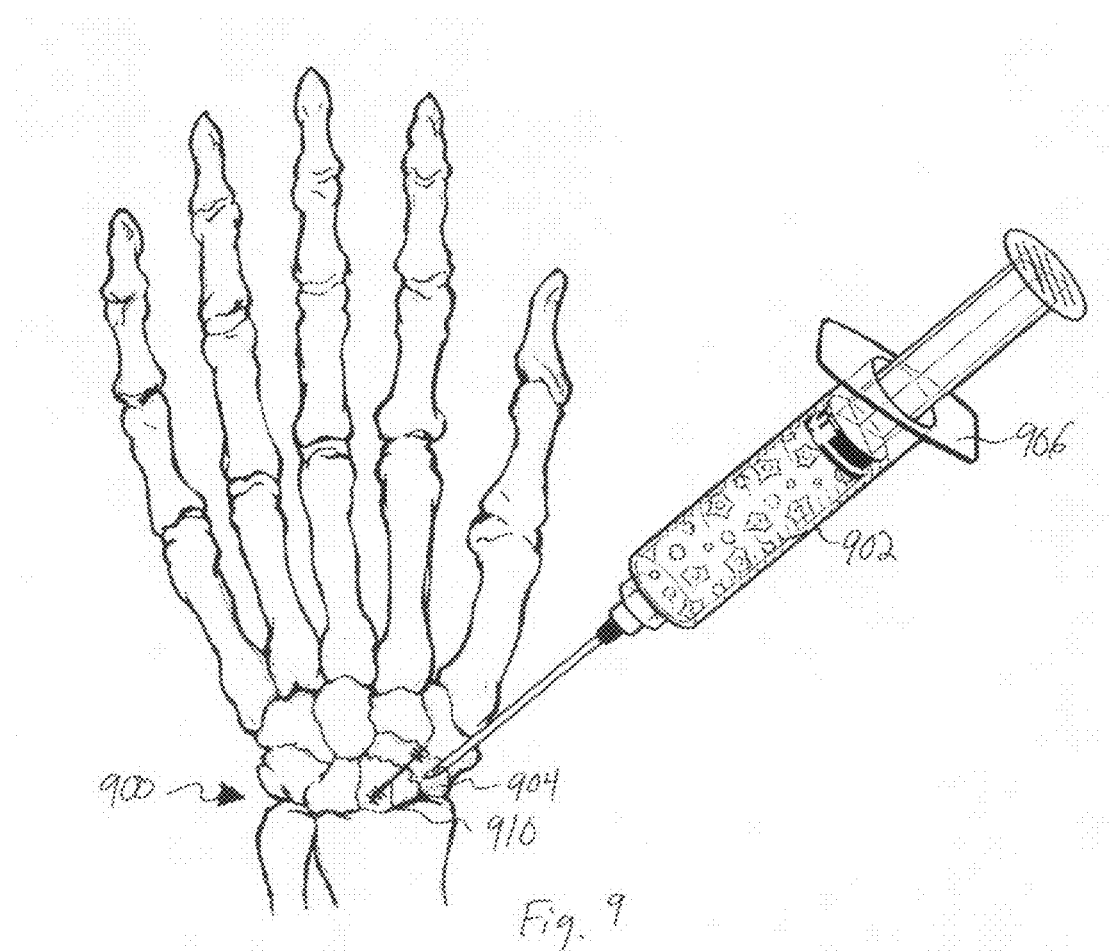
Fig. 9
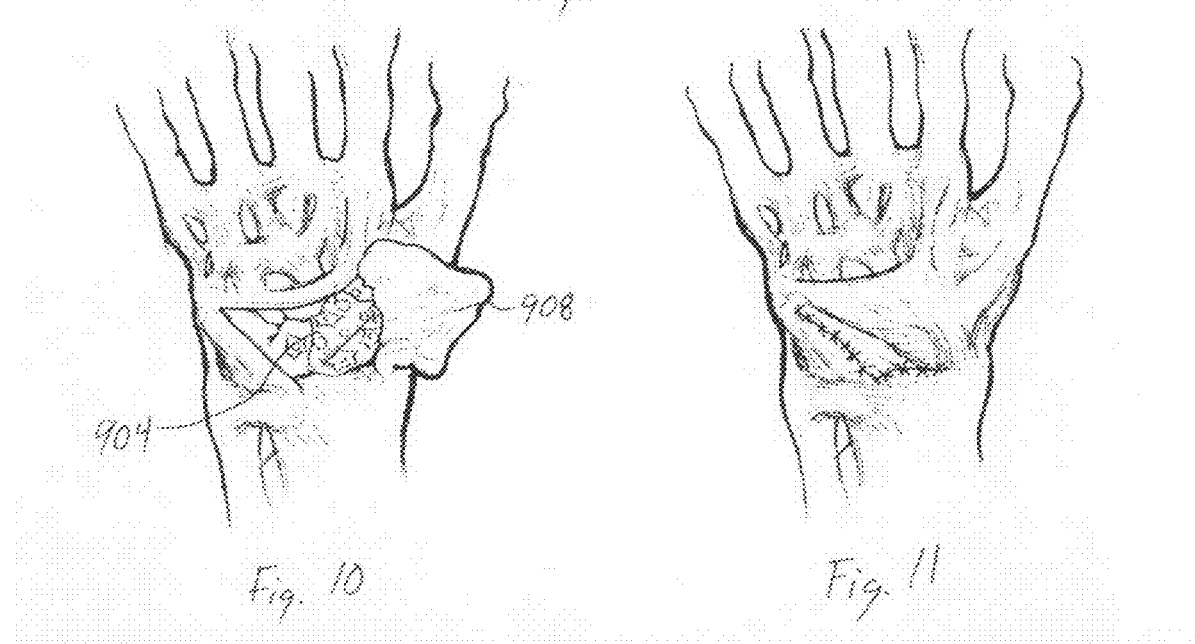
Fig. 10
Fig. 11

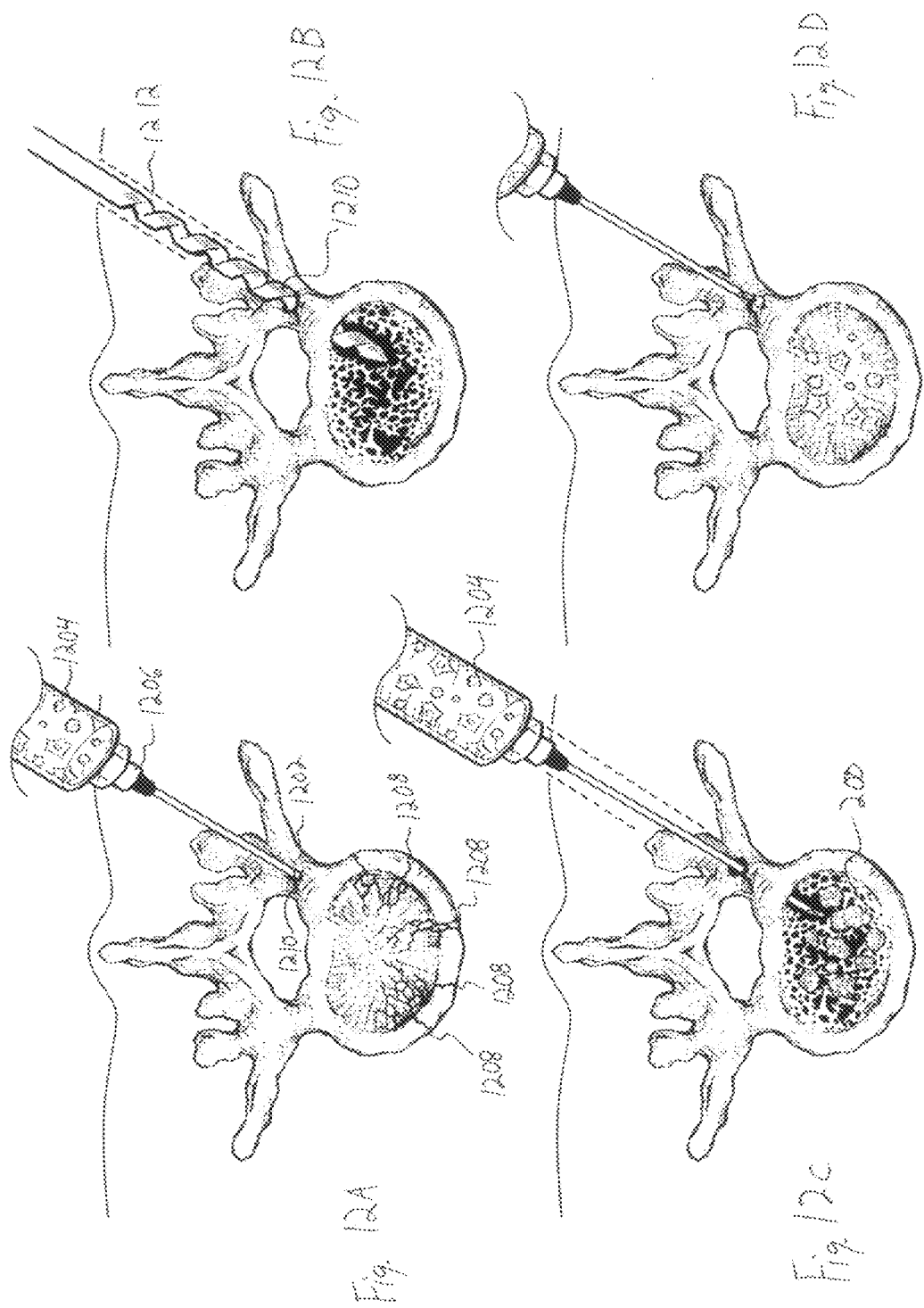

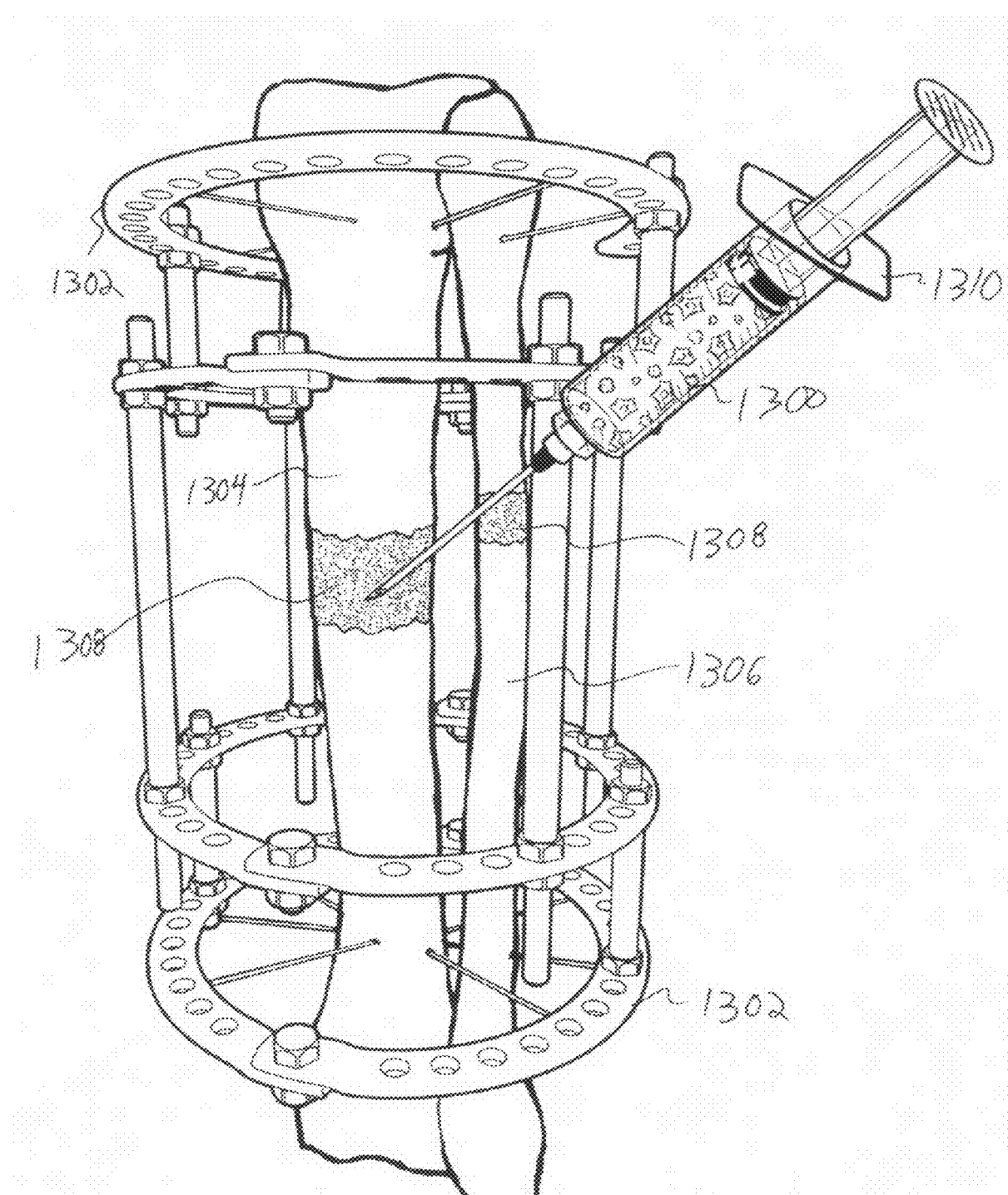

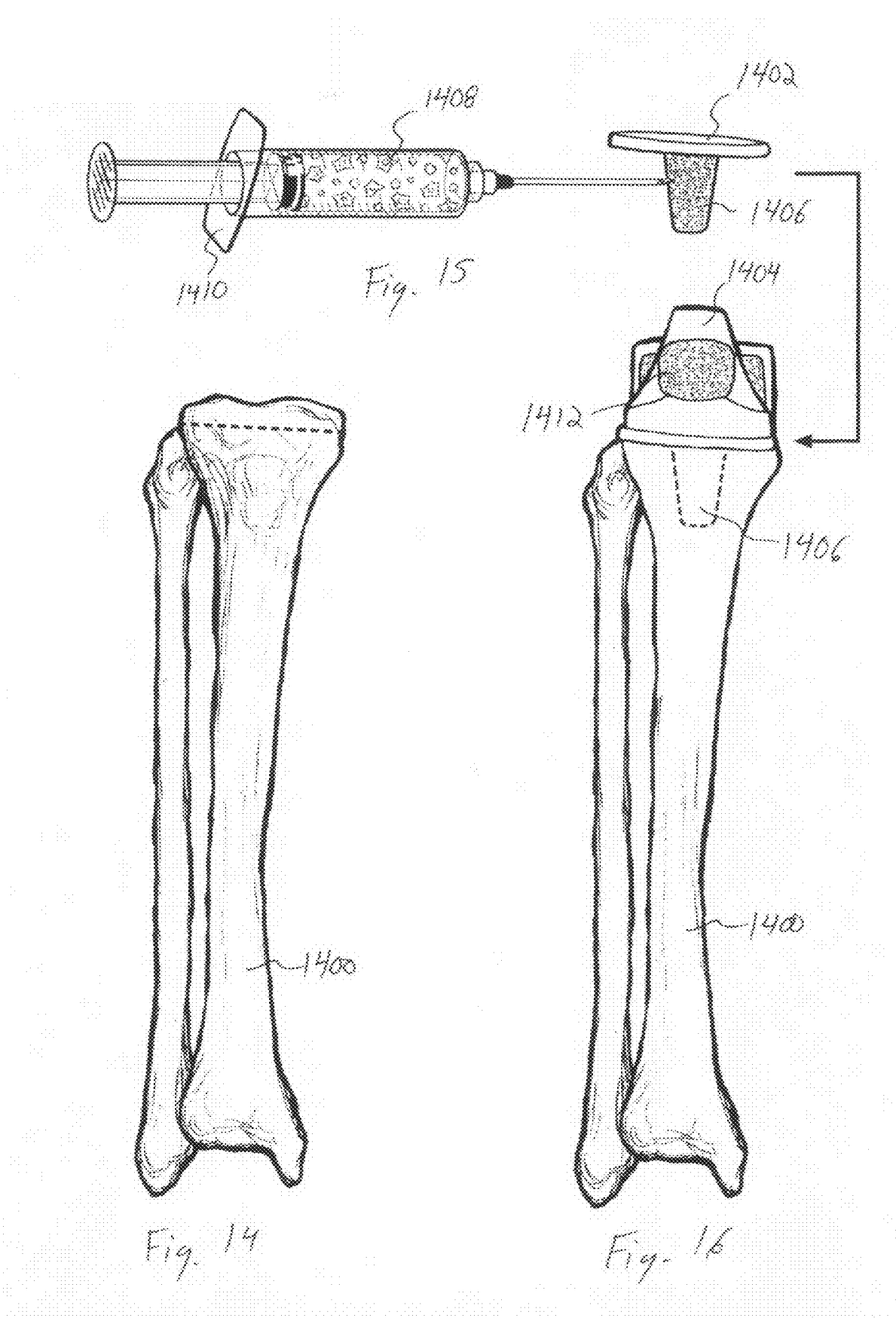

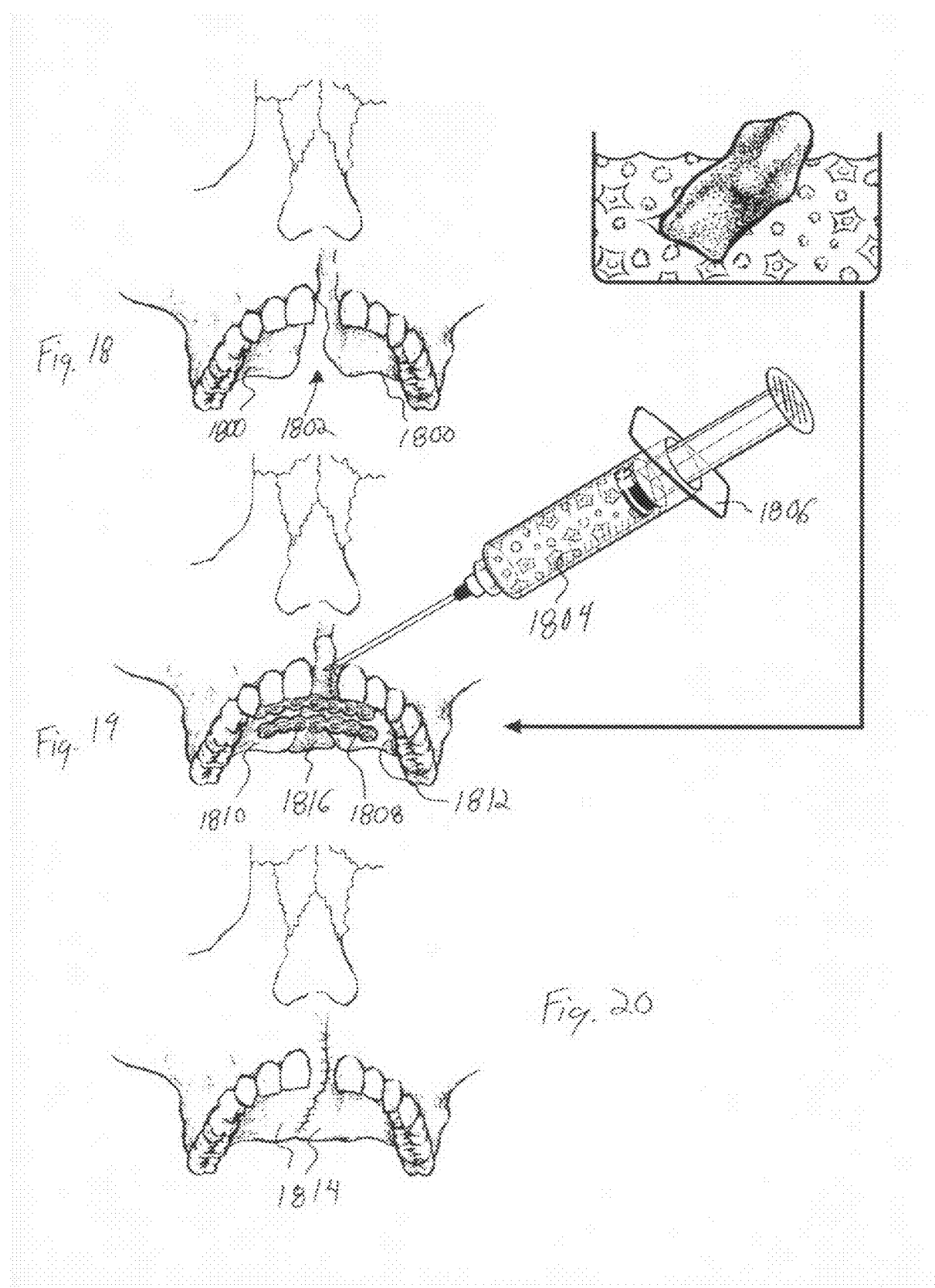

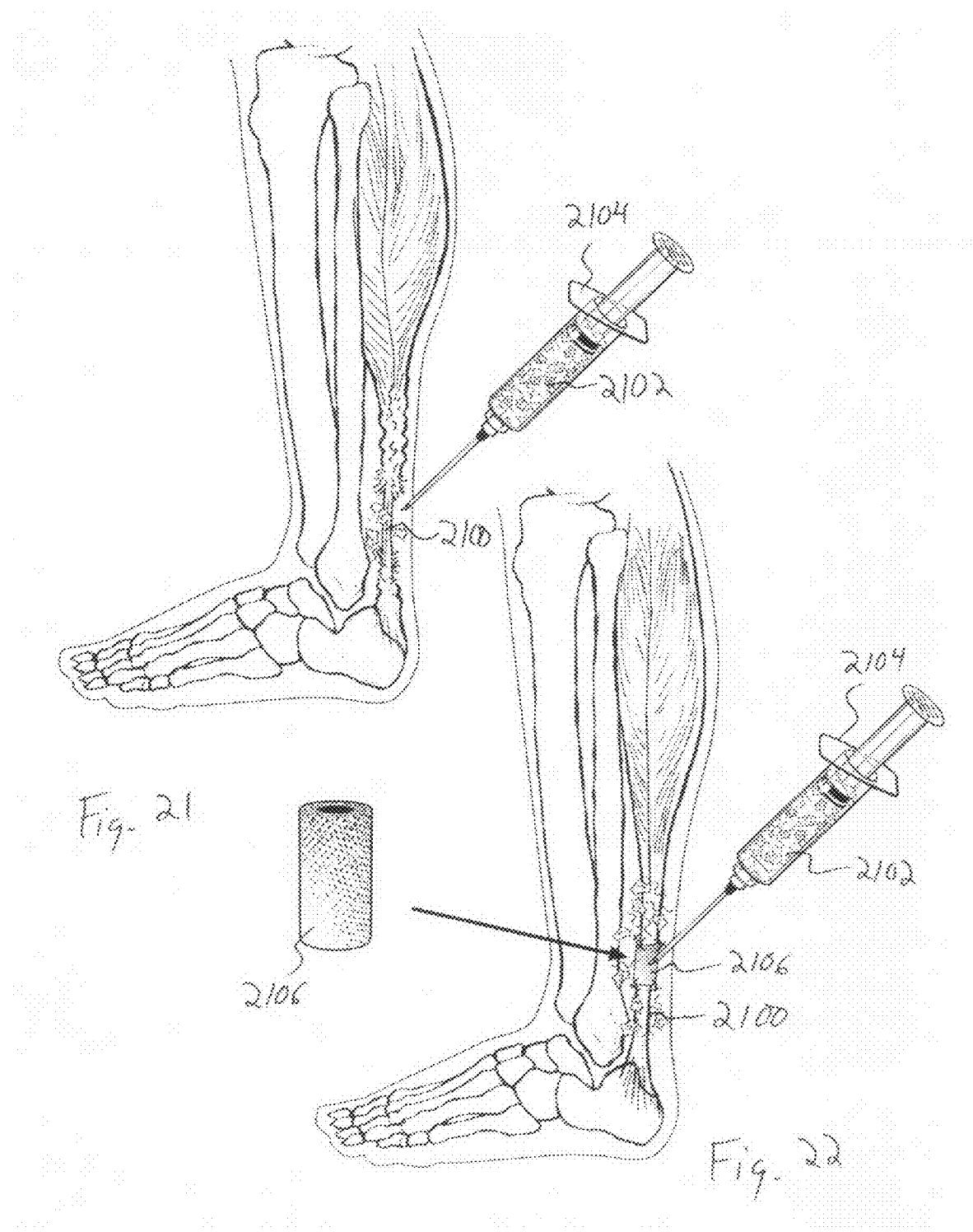

ENHANCED MEDICAL IMPLANT COMPRISING DISRUPTED TOOTH PULP AND TOOTH PARTICLES

CROSS-REFERENCE TO RELATED APPLICATIONS

This application is a continuation-in-part of, and claims priority to, U.S. patent application Ser. No. 12/348,280, filed on Jan. 3, 2009 now abandoned, the disclosure of which is hereby incorporated by reference.

RELATED ART

1. Field of the Invention

The present disclosure relates to harvesting stem cells from teeth and thereafter using the harvested stem cells and parts of the tooth, such as soft tissue, to create medical implants that are compatible with the mammalian body.

2. Brief Discussion of Related Art

Scientific Progress and Future Research Directions (June 2001), indicate that sources of stem cells include bone marrow, peripheral blood, blood vessels, the cornea and the retina of the eye, brain, skeletal muscle, dental pulp, liver, skin, the lining of the gastrointestinal tract, and pancreas. Methods and apparatus have been developed to remove stem cells from some of these areas of the mammalian body. As to removal of stem cells from bone material specifically, such methods and apparatus include U.S. Patent Publication No. 2008/0176325 to Bowermaster, et al., the contents of which are incorporated herein by reference.

INTRODUCTION TO THE INVENTION

Referring to FIGS. 1 and 3, harvesting dental pulp from a tooth 100 requires dissecting or opening the tooth to reveal the molar pulp and stem cells 124, or otherwise manipulating the pulp to remove it from the pulp chamber 120 and root canal 122. The pulp can be separated into a soft tissue connective tissue 134 and stem cells 136. Thereafter, the stem cells 136 may be combined with one or more of the following: processed soft tissue 134 (shown in test tubes); ground hard aspects 138 of the harvested tooth 100; other autologous patient tissues; autologous blood concentrates; growth factors; autologous biologic bone particles or a matrix; and a synthetic biocompatible graft material or scaffold. In this respect, this disclosure provides a means for harvesting stem cells from the pulp of teeth (and other cells and tissues which may be found in the removed tooth) and utilizing these harvested materials for medical objectives. Such medical objectives include, without limitation, fostering or accelerating bone ingrowth and joint repair, reconstruction or reconstitution. Such medical devices also include fostering or accelerating connective tissue regrowth and repair, and fostering or accelerating non-connective tissue regrowth and repair.

Pursuant to the instant disclosure, orthopedic implants may be created that have true bone ingrowth capabilities, thereby obviating the need for cement or other artificial adhesion techniques. Other exemplary bone repair, reconstructive, and regeneration uses within the scope of the instant disclosure include fracture treatment, fracture non-union treatment, bone fusions, bone lengthenings, bone defect repair, bone osteotomies and other orthopedic, maxillofacial, orthodontic human and veterinary applications.

In addition to these bone uses for repair, reconstruction, and reconstitution, the products and implants of the present disclosure may be used in combination with tooth collagen and tooth connective tissue for soft tissue and joint applications. Dental pulp stem cells combined with tooth tissue collagen and connective tissue may be utilized for a variety of clinical purposes including wound treatment, hemostasis, nerve repair, joint cartilage and meniscal repair, ligament and tendon and soft tissue augmentation, repair and reconstruction. Soluble stem cell collagen and tooth soft tissue products may be used as a subcutaneous implant for repairing dermatological defects such as acne scars, glabellar furrows, excised scars and other soft tissue defects.

The present disclosure also provides bone or soft tissue ingrowth through cell migration into the interstices of a tooth derived collagen or connective tissue 142 or ground tooth particulate matrix 144. In exemplary form, the tooth derived collagen 142 or ground tooth particulate matrix 144 may have varying degrees of porosity to create a skeleton providing sufficient interstices and volume for cells to attach and grow into the matrix, and to synthesize their own macromolecules. These attached cells then produce the desired new matrix characterizations, which allows for the growth of additional new tissue for the particular, specific application.

Additives such as hyaluronic acid and fibronectin may augment the soft tissue implants of the present disclosure. Hyaluronic acid in a collagen matrix, for example, encourages cellular infiltration into the pores and channels of the matrix. Fibronectin, on the other hand, induces cell attachment to fibers of a collagen matrix, for example. Autologous and allogenous blood concentrates and tissue derivatives 154 can also be added to the dental pulp derived products to enhance their function, viability, and incorporation.

In a first exemplary embodiment, the present disclosure relates generally to a composition comprising a collection of pluripotent stem cells collected from the dental pulp of a harvested human tooth (such as a third molar), whether or not the stem cells have been duplicated or purified (i.e., cell passes), in combination with at least a portion of a processed mammalian tooth (hard and/or soft components of the tooth, such as enamel and connective soft tissue within the tooth and pulp segments).

In a second exemplary embodiment, the present disclosure relates generally to a medical implant composition comprising a collection of pluripotent stem cells collected from the dental pulp of a harvested human tooth, whether or not the stem cells have been duplicated or purified (i.e., cell passes), in combination with at least a portion of a mammalian tooth and a synthetic particulate or synthetic matrix formed comprising at least one of a porous biocompatible metal (porous tantalum and porous titanium), a biocompatible thermoplastic, a biocompatible thermoset, and a ceramic based biocompatible mineral (Demineralized bone matrix, calcium phosphates (e.g., Hydroxyapatite (HA) and β-tricalcium phosphate) calcium sulfate composites (e.g., OsteoGraf [DENTSPLY Friadent CeraMed, Lakewood, Colo.], Norian SRS [Synthes, Inc, West Chester, Pa], ProOsteon [Interpore Cross International, Irvine, Calif.], Osteoset [Wright Medical Technology, Inc, Arlington, Tenn.]) and degradable and non-degradable polymer-based bone graft substitutes, (e.g., Cortoss [Orthovita, Inc, Malvern, Pa.], open porosity polylactic acid polymer [OPLA], Immix [Osteobiologics, Inc, San Antonio, Tex.]).

In a third exemplary embodiment, the present disclosure relates generally to a bone graft slurry comprising a collection of pluripotent stem cells collected from the dental pulp of a harvested human tooth, whether or not the stem cells have been duplicated or purified (i.e., cell passes), in combination with at least a portion of a ground, particulate mammalian tooth.

In a fourth exemplary embodiment, the present disclosure relates generally to a collagen slurry comprising a collection of pluripotent stem cells collected from the dental pulp of a harvested human tooth, whether or not the stem cells have been duplicated or purified (i.e., cell passes), in combination with at least a portion of a soft tissue component from the mammalian tooth papilla.

In a fifth exemplary embodiment, the present disclosure relates generally to a method of forming a biologic matrix implant, comprising the steps of: processing at least a portion of a mammalian tooth to form particulate matrix; combining the particulates from the mammalian tooth with a collection of pluripotent stem cells collected from the dental pulp of a harvested hu man tooth, whether or not the stem cells have been duplicated or purified (i.e., cell passes), to form a biologic matrix implant.

In a sixth exemplary embodiment, the present disclosure relates generally to a method of forming a biologic matrix implant, comprising the steps of: processing at least a portion of a mammalian tooth to form particulates; combining the particulates from the mammalian tooth with a source of hydroxyapatite to form a biologic matrix; and, combining the biologic matrix with a collection of pluripotent stem cells collected from the dental pulp of a harvested human tooth, whether or not the stem cells have been duplicated or purified (i.e., cell passes), to form a biologic matrix implant.

In a seventh exemplary embodiment, the present disclosure relates generally to a method of forming a biologic matrix, comprising the steps of: processing at least a portion of a mammalian tooth to form particulates; and, combining the particulates from the mammalian tooth with a source of hydroxyapatite to form a biologic matrix.

In an eighth exemplary embodiment, the present disclosure relates generally to a soft tissue composition of matter comprising: a collection of pluripotent stem cells collected from the dental pulp of a harvested human tooth, whether or not the stem cells have been duplicated or purified (i.e., cell passes); and, connective tissue harvested from the dental pulp of a harvested human tooth.

In a ninth exemplary embodiment, the present disclosure relates generally to a method of forming a soft tissue replacement comprising: collecting pluripotent stem cells from dental pulp of a harvested human tooth, whether or not the stem cells have been duplicated or purified (i.e., cell passes); collecting connective tissue harvested from the dental pulp of a harvested human tooth; and, combining the harvested connective tissue with the harvested pluripotent stem cells to form an HLA matched soft tissue replacement.

In a tenth exemplary embodiment, the present disclosure relates generally to a medical implant composition comprising: a collection of pluripotent stem cells collected from the dental pulp of a harvested human tooth; at least a portion of a mammalian tooth; and, an autologous biological matrix formed from a source selected from the group consisting of the harvested tooth, bone from an autologous donor, and soft tissue from the donor.

In an eleventh exemplary embodiment, the present disclosure relates to a method of making an HLA ABO matched or unmatched allograft medical implant, comprising: removing a human tooth from a donor; harvesting pluripotent cells from the pulp of the tooth; cryogenically preserving the pluripotent cells and the tooth; pulverizing the tooth to form a bone powder therefrom; forming a bone matrix from the tooth powder; and, combining the pluripotent cells and the matrix to form an allograft medical implant.

In a twelfth exemplary embodiment, the present disclosure further relates to a method of fabricating a medical implant, comprising: removing a human tooth from a donor; harvesting pluripotent cells from the pulp of the tooth; cryogenically preserving at least one of the pluripotent cells and the tooth; pulverizing the tooth to form a bone powder therefrom; forming an autologous bone particulate matrix from the tooth powder; and, combining the pluripotent cells and the particulate matrix to form the implant.

In a thirteenth exemplary embodiment, the present disclosure further relates to a method of fabricating a soft tissue medical implant, comprising: removing a human tooth from a donor; harvesting pluripotent cells from the pulp of the tooth; cryogenically preserving the pluripotent cells and the tooth; separating the pulp stem cells from the surrounding collagen and soft tissue; forming an autologous collagen or connective tissue matrix from these tooth tissues; and, combining the pluripotent cells and the matrix to form the soft tissue medical implant.

BRIEF DESCRIPTION OF THE DRAWINGS

FIGS. 9-11 include a series of figures showing a human scaphoid fracture and how the scaphoid fracture is treated with stem cell molar bone graft slurry and THA, and thereafter enclosed, to facilitate bone formation at the fracture site.

FIG. 12 is a top, plan view of a human vertebrae being injected with stem cell molar bone graft slurry to treat vertebral fractures and osteoporosis.

FIG. 13 is a frontal view of an Ilizarov device distracting an osteotome site of the lower leg of a human, where the osteotome site is augmented with stem cell molar bone graft slurry.

FIG. 14 is a frontal view of human lower leg bones, the fibula and tibia.

FIG. 15 is a profile view showing the general injection and bonding site for a stem cell slurry on a prosthetic tibial tray having a porous stem.

FIG. 16 is a frontal view of human lower leg bones, the fibula and tibia, where a total knee arthroplasty procedure has been carried out using a cementless femoral and patella components, and the cementless tibial tray of FIG. 15 implanted into the tibia.

FIGS. 18-20 include a series of figures showing a human cleft palate and how the cleft palate is treated with stem cell molar bone graft slurry and custom 3-D matrix, and thereafter enclosed, to facilitate bone formation at the cleft palate site.

FIG. 21 is a profile view of a human lower leg showing certain bones, muscles, and a partially torn Achilles tendon.

FIG. 22 is a profile view of a human lower leg showing certain bones, muscles, and a torn Achilles tendon, where the torn Achilles tendon is treated with a stem cell soft tissue slurry and pulp soft tissue derived matrix formulated in accordance with the instant disclosure.

DETAILED DESCRIPTION

The exemplary embodiments of the present disclosure are described and illustrated below to encompass harvesting stem cells from teeth and thereafter using the stem cells in addition to other tooth material to create medical implants and therapeutic compositions such as tissue growth accelerators or regeneration formulations that are compatible with the mammalian body. Of course, it will be apparent to those of ordinary skill in the art that the exemplary embodiments discussed below may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure. For example, the devices and methods disclosed are applicable to all manner of medical implants anatomies, including spine, knee, hip, shoulder, elbow, skull, maxilla, and the like.

Figure 3:
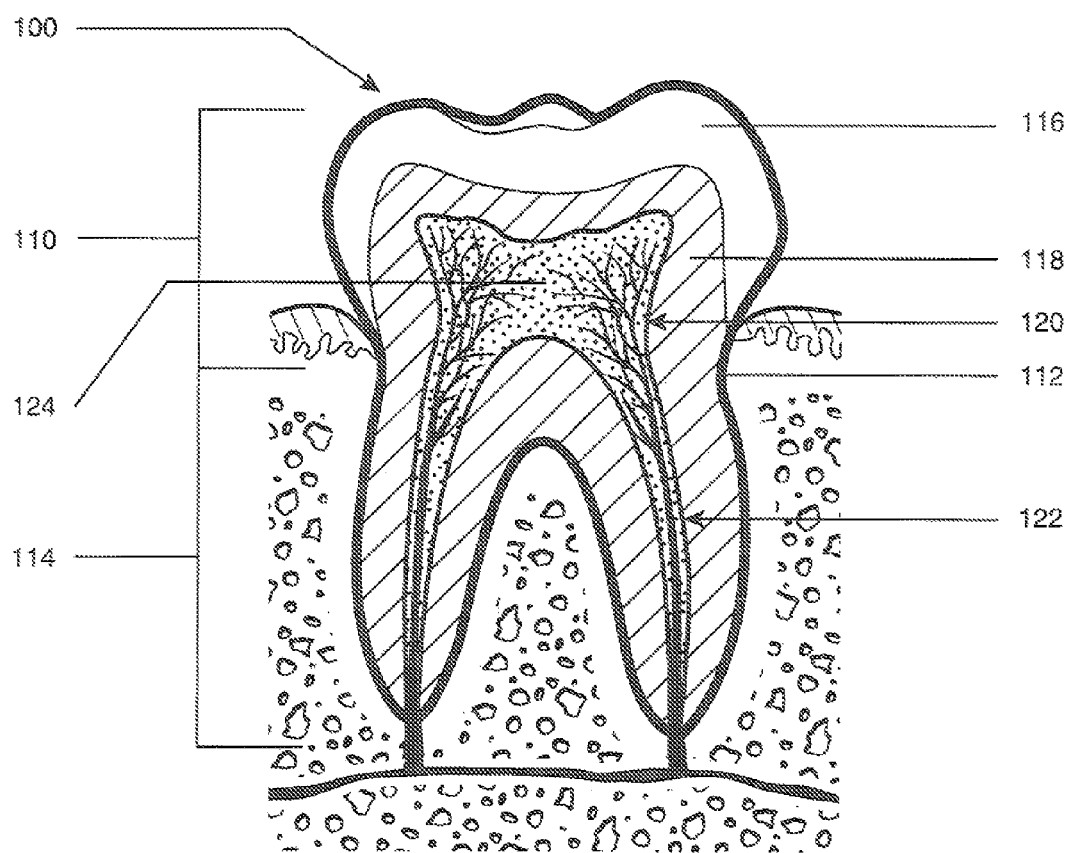
FIG. 3 is a cross section of a mammalian molar tooth taken vertically.

Referencing FIG. 3, an erupted human tooth 100 anatomically includes a crown 110, a neck 112, a root 114, enamel 116, dentin 118, a pulp cavity 120, and a root canal 122. Pluripotent stem cells may be located within the pulp cavity 120 of a mammalian tooth, specifically the pulp cavity 120 of unerupted wisdom teeth (see FIG. 17, numeral 1732). An exemplary method of harvesting stem cells from molar teeth as disclosed in U.S. Patent Publication 20080176325 to Bowermaster, et al., the disclosure of which is incorporated herein.

The primary difficulties encountered with harvesting stem cells from sources other than dental pulp has been a more limited number of cells and relatively high degree of difficulty culturing and growing the isolated cells. In contrast, molar dental pulp normally contains millions of stem cells. These cells are relatively homogeneous and exhibit markers associated with embryonic stem cells. In addition to stem cells, the harvested molar tooth pulp also includes connective tissue cells that are relatively easy to culture and reproduce.

Stem cells can be readily obtained by isolating the developing dental pulp or mesenchymal dental papilla from an unerupted tooth bud such as, for example, an unerupted third molar. A tooth bud is a knoblike primordium that develops into an enamel organ surrounded by a dental sac, encasing the dental papilla. Dental papilla is a mass of mesenchymal tissue that ultimately differentiates to form dentin and dental pulp. The dental sac ultimately differentiates to form the periodontal ligament. For each unerupted tooth, a tissue mass can be isolated to provide two to five million stem cells. As used herein, "isolated" or "isolating" refers to removal of the tissue mass containing stem cells from the oral cavity of a mammal, including a human.

Tooth buds appear in early childhood, with the last, the third molar, beginning to form at approximately four years of age in a human. By the time the twenty deciduous teeth have erupted in a human, the first permanent molars have also erupted or are erupting. There are approximately twenty-eight tooth buds for permanent teeth in various states of development in the tissue beneath the deciduous teeth. By the time the molar teeth erupt, the enamel organ has generally encased the dental pulp. Prior to eruption, however, the mesenchymal tissue may be surgically removed to provide an isolated tissue comprising millions of stem cells. It is to be understood, however, that any tooth bud or unerupted mammalian tooth may provide an isolated tissue for extraction of stem cells according to the present disclosure.

As mentioned previously, an attractive source of isolated tissue is an unerupted third molar. This is particularly the case since this developing tooth is often surgically removed without negative consequences to the patient. In addition, it is known that stem cells from third molars may differentiate into osteoblasts (*Osteogenic potential molar stem cells alone*, J. Oral Maxillofac Surg. 2009 Mar., 67(3):501-6; *Evaluation of pluripotency in human dental pulp cells*, Koyama N, et al., Pharmacogenomics J., 2009 Sep. 1, PMID: 19721467; *Isolation and characterization of stem cells derived from human third molar tooth germs of young adults: implications in neo-vascularization, osteo-, adipo- and neurogenesis*, Yalvac M E, et al, The Pharmacogenomics Journal advance online publication, 2009 Sep. 1).

Third molars, often called "wisdom teeth," generally erupt between the ages of 17 and 21 in a human. Second molars usually erupt between the ages of 11 and 13 in a human, but allow during this time frame detection of developing third molars by x-ray or other imaging devices. If there is insufficient room for the third molar or it is developing abnormally (e.g., some third molars appear to be growing "sideways" in maxilla or mandible), the third molar may be surgically removed before it becomes impacted (which may occur if the developed tooth has not reached its appropriate final position by adulthood) or causes misalignment of other teeth.

Third molars are customarily removed from pre-teen and teenage patients while the molars are still developing, and while the primordial bulb still contains millions of stem cells. Third molars may be extracted from living humans, as well as juveniles that are deceased proximate the time of death. In particular, just as an organ transplant donor may provide viable organs proximate the time of death, the same donor (presuming a juvenile) may provide one to four third molars from which stem cells may be harvested consistent with the instant disclosure. Hydroxyapatite (HA), having a chemical formula of $Ca_{10}(PO_4)_6(OH)_2$, is the main mineral constituent of human bone and human teeth, and is an outstanding bone substitute because of its osteoconductive properties.

Human Derived Tooth Hydroxyapatite (THA) may be used as a bone graft substitute. In ashed or calcinated form, the natural bioceramic THA is very successful in promoting osteointegration. THA is also a safe bone-graft bioceramic material for bone grafting. THA can be formed into powders and particulate, just like other sources of hydroxyapatite currently being used (e.g., HA ceramics can be manufactured from natural materials such as coral to create scaffolds or matrices. Any of these THA derived forms allow for enhanced osteointegration when combined with the associated dental pulp stem cells.

Teeth, such as third molars, that are discarded during the normal dental cycle could also be stored or cryopreserved for later combination with third molar THA to increase the amount a graft material available. Since approximately 800,000 third molars (generally the last set of teeth to erupt) are removed each year in the United States alone, the number of available stem cells is not insignificant. Removal of four third molars from a single donor can easily yield eight to over twenty million multipotent (i.e., pluripotent) stem cells. A majority of these stem cells harvested from teeth, particularly third molars, are Oct4 positive, SSEA1 positive, SCA1 negative, MART-1 negative, TRA80-1 positive, SSEA-4 negative, CD117 negative and TRA60-1 negative, indicating that the stem cells are primitive, multipotent cells that may be induced to differentiate into a variety of cell and tissue types.

In a preferred circumstance, one or more teeth are extracted from the intended recipient of the medical implant or therapeutic stem cell compositions in order to create an autologous dental pulp stem cell product. In such a circumstance, the stem cell donor and bone or soft tissue graft patient are the same person. However, siblings and other individuals closely related to the intended recipient (sometimes referred to herein as the "patient") in need of dental pulp stem cell product(s) combined with other tooth components may qualify as tooth stem cell donors. Other mammalian patients and related donors have similar tooth derived stem cell product compatibility.

Referring to FIG. 3, as an example, harvesting stem cells from teeth usually follows extraction of the entire tooth from an oral cavity. After the tooth 100 is removed, each tooth surface is cleaned and a circumferential cut is made through any enamel 116 and dentin 118 proximate the crown 110 of the tooth, thereby allowing the crown 10 to be separated from the root 114. Cutting through the enamel 116 and dentin 118, followed by removal of the crown 110, is operative to expose the pulp cavity 120 and molar pulp and stem cells 124 contained within the pulp cavity. Alternatively, the molar pulp and stem cells 124 may be enucleated from the hard or solid portions of the tooth, such as the third molar.

Figure 1:
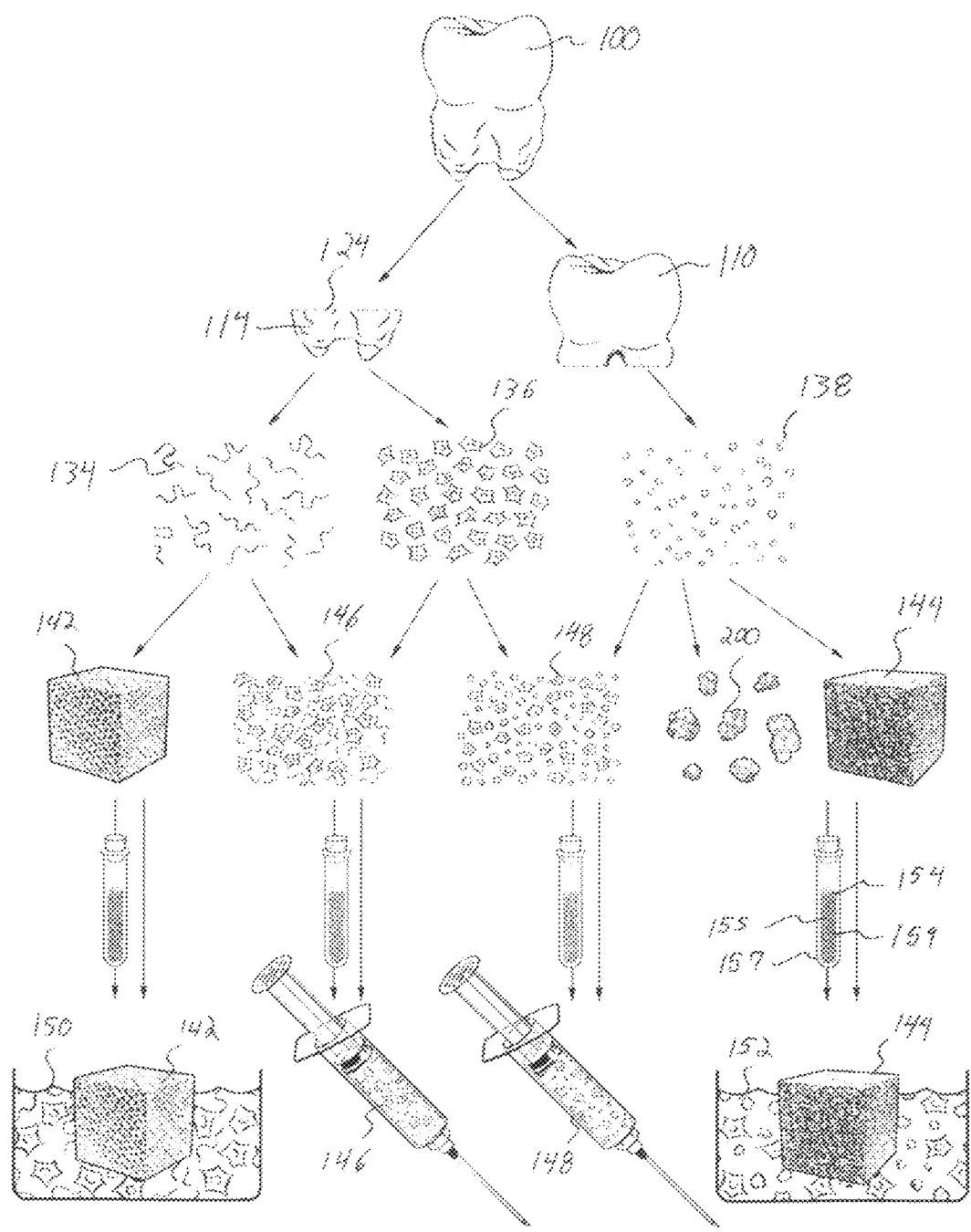
FIG. 1 is a schematic diagram showing the sequence of utilized to transform a harvested tooth into a multitude of intermediates (stem cells, mineral and soft-tissue components) and thereafter a multitude of products.

Referencing FIG. 1, the resulting molar pulp and stem cells 124 removed from the pulp cavity 120 are processed for future use. In one exemplary sequence, after the molar pulp and stem cells 124 are removed, this mixture is subsequently added to a solution of 3 mg/ml collagenase type I and 4 mg/ml dispase for approximately 60 minutes at an ambient human body temperature of 98.6° F. The resulting product is a slurry, which is strained to remove the stem cells 136 from solution, with the separated stem cells being available for immediate use or available for cryogenic preservation. The collagen portion 134 is also separated (and expanded if necessary) from the resulting slurry and may be used to create a mixture 146 of collagen and stem cells for soft tissue applications. Alternatively, the molar pulp and stem cells 124, which includes the connective pulp tissue, is diced without collagenase digestion for immediate use or cryogenically banked.

In one exemplary variation, the stem cells 136, connective tissues 134, and tooth 110 are cryogenically banked using human leukocyte antigen (HLA) typing for future autologous and/or therapeutic uses. Dental pulp stem cells, if used in bulk without duplication or cell passes, may require HLA typing for allogenic use. It is to be understood, however, that HLA typing need not be required for autologous and therapeutic uses in circumstances where extracted stem cells comprise a pure mesenchymal isolate. For example, a pure mesenchymal isolate from the dental pulp has no immunogenicity and may be included with ground or otherwise processed tooth from an un-HLA matched allograft host source. Simple blood typing (e.g. A, B, AB, O) is adequate for many mammals.

Those skilled in the art will recognize that use of a single autologous donor for the stem cells and the bone and soft tissue graft source has the advantage of reducing or eliminating the risk of the mammalian body rejecting the medical implant and therapeutic stem cell compositions. Of course, it is also within the scope of the disclosure to utilize multiple donors. Where multiple donors are used as the source of either the stem cells or the bone graft material (such as a ground tooth) or the soft tissue material, these donors and patients can be matched using standard known matching means, such as, without limitation, HLA typing. HLA are proteins, or markers, found in most cells of a mammalian body and used to differentiate between native and foreign cells.

A close match between a patient's HLA markers and those of one or more donors reduces the risk that the patient's immune cells will attack the donor's cells. Moreover, a close HLA match improves the chances for graft incorporation and vascularization. Engraftment occurs when the donated cells start to grow and make new blood cells, which reduces the risk of a post-transplant complication called graft-versus-host disease (GVHD). GVHD occurs when the immune cells from the donated graft attack the host body. If a patient is in need of an allogenic implant (which uses cells from a family member, unrelated donor or cord blood unit), a doctor simply takes a blood sample to test the patient and donor for HLA type. When a donor tooth and attached cells are harvested, blood can be drawn and sent for HLA typing to make possible allogenic fresh or cyropreservation grafting.

Those skilled in the art are familiar with sterilization preservation techniques for stem cells. The dental pulp stem cells, if enucleated (such as from a harvested, unerupted third molar), can have the surface sterilized with antiseptic solutions (alcohol, betadine, etc). Cell loss to certain depths occurs depending on the solution chosen and the length of time exposed to the antiseptic. Many commercially available products can sterilize the harvested stem cells and connective tissue for bacterial, viral and even for mycoplasm contamination (e.g., BIOMYC-2 is based on minocycline, which is a tetracycline derivative; BIOMYC-3 is based on the ciprofloxacin antibiotic, which is a member of the fluoroquinolone group). As discussed briefly beforehand, the dental pulp may also be minced and a separation (e.g., collagenase) process carried out to divide the pulp into stem cells and connective tissue prior to storage. Alternatively, a tooth or teeth may be decontaminated en mass with stem cell containing pulp attached and subsequently cryopreserved intact. In any event, different sterilization methods may be required for each of these different protocols. Also, oral decontamination (e.g., Chlorhexidine) and other antiseptic techniques used during molar harvesting are operative to decrease the extent of bacterial contamination and reduce the sterilization required, which in turn lessens the loss of stem cells in the processing and storage phases.

Stem cells harvested fresh will, after decontamination, need to be temporarily or long-term preserved to maintain stem cell viability. Those skilled in the art are familiar with preservation techniques for stem cells. Temporary preservation after initial sterilization can be done with various solutions depending on the time before use or storage. Aedesta Cryopreservation Medium was originally developed for organ preservation by Lifeblood Medical, Inc., as Lifor, and optimized by Cell Preservation Solutions, LLC. Other solutions have isotonic concentration to closely match the human body. Phosphate buffer saline (PBS) is a buffer solution commonly used in biochemistry and has many uses because it is isotonic and non-toxic to cells. PBS is a salty solution containing sodium chloride, sodium phosphate, and potassium phosphate. In addition to the correct choice of solution, depending on the time to use, various amounts of cooling and refrigeration may also be employed to insure maximum stem cell viability. This includes long-term preservation and cryopreservation. See *Optimized cryopreservation method for human dental pulp-derived stem cells and their tissues of origin for banking and clinical use*, Woods E J, et al., Cryobiology, 2009 October; 59(2):150-7, the contents of which are incorporated herein by reference.

Those skilled in the art are also familiar with in vitro multiplication of stem cells. European Patent EP1557461 details the ability to proliferate or establish undifferentiated pluripotent stem cells that retain their differentiation potency by culturing pluripotent stem cells in a medium free of a feeder cell, or a serum. Serum media are available from various manufacturers specializing in marrow mesenchymal stem cell (MSC) passage (e.g. IVGN has recently released a reduced serum medium formulation MesenPRO RS (IVGN Cat. # 12746012)) optimized for the expansion of human MSCs through multiple passages while maintaining their ability to differentiate into chondrogenic, osteogenic and adipogenic lineages. The aim is attained by using a culture medium for pluripotent stem cells comprising the known ingredients, which is supplemented with an inhibitor of an adenylate cyclase activity.

An exemplary technique for expanding cryopreserved stem cells (http://ink.primate.wisc.edu/~thomson/protocol.html#thawing) involves first removing the molar pulp stem cells from a liquid nitrogen storage tank. The cryovial is gently swirling in water bath until only a small ice pellet remains. Then the cryovial is completely submerged in 95% ethanol for final thawing. The cells are then gently pipetted from the vial into a conical centrifuge tube. Media is slowly added drop wise to reduce osmotic shock. While adding media, the cells are gently mixed in the tube by gently tapping the tube (with a finger). Then, the cells are centrifuged for a predetermined time, with an optional intermediate resuspension phase, followed by re-centrifugation. The cells are then resuspended in 2 mL and add 0.5 mL per well of a 4 well plate that has MEFs already plated on it. The media is changed daily. The cells are then expanded on Matrigel-coated plates (kept throughout the process). The human molar stem cells grow until the colonies are large and the cells are piled up ready for splitting. The cells can then be spit on Matrigel. Matrigel Aliquoting and plated stem cells need to be fed everyday with a standard hES media. Differentiated cells should be picked off of the plate if more than 5% of the culture is differentiated.

It should be noted that the tooth from which the stem cells are extracted might also be preserved. After the stem cells are extracted from the tooth, the tooth is bathed in an antiseptic solution, followed by a deproteinizing bathing in an alkali solution (1% concentration of sodium hypochloride) for several hours. The enamel and dentin can be separated sharply by various cutting methods. Alternatively, a high temperature baking process (850° C. for 2-3 hours) follows extraction of the tooth from the alkali solution to calcinate the tooth. At high temperatures, the dentin matter and enamel matter separate easily and provide a separation approximately 60% dentin and 40% enamel. This high temperature baking process is also operative to sterilize the tooth and provide human hydroxyapatite free from infectious processes that have previously hindered utilization of human hydroxyapatite, such as hepatitis B.

For example, calcinated sheep teeth have been used a bone graft material. See, F. N. Oktar, et al "Histopatological evaluation of tooth derived hydroxyapatite and plaster of Paris as grafting material in rabbits," *Proceedings of the National Biomedical Engineering Symp. of Biyomut* 97, pp. 54-61, 1997, the disclosure of which is incorporated herein by reference. Calcinated teeth have also been used as a human bone-derived hydroxyapatite (HHA) plasma-spraying powder. In a similar exemplary application, powderized autologous THA could be plasma-sprayed onto an implant ingrowth interface and then autologous stem cells or slurry applied to optimize bone ingrowth. The starting powder is derived using the calcinations method as described in the following references, EP0489728 and WO9001955, the disclosures of each of which are incorporated herein by reference.

It should be noted that the tooth from which the stem cells are extracted might also be preserved in addition to, or independent of, the stem cells. The donor tooth may be preserved in whole (which includes the two primary parts comprising the removed crown 110 and lower root 114 (see FIG. 1)) or segmented into smaller pieces, such as by grinding. Also, deciduous teeth shed during the normal dental cycle could also be saved and cryopreserved. Regardless of how the residual tooth is to be preserved, the tooth is initially bathed in an antiseptic solution. Further processing may take place after bathing the tooth in the antiseptic solution. For example, the tooth may be bathed in an alkali solution for several hours, followed by a baking process to calcinate the tooth, as discussed above, so that the enamel and dentin may be separated and preserved separately. Alternatively, the hard components of the tooth may be dried after withdrawal from the aseptic solution and preserved at room temperature in a sealed container.

Prior to, or subsequent to, tooth preservation, the tooth may be ground to create tooth particles of various size ranges. For example, dentin may be ground to have particle sizes ranging between 100-150 μm. By way of example, and not limitation, the molar tooth may be ground to have mean particle sizes in the range of 5-100 μm, 100-500 μm, and 500-1,000 μm. Referencing FIG. 12, bone graft slurries 1204 for sub-cutaneous needle guided injection 1206 into highly contained areas (vertebral body fracture, see FIG. 12A) generally have a 5-100 μm particulate size. Known milling and other techniques exist to sterilely process hard tissues, such as bone and teeth, to various dimensions (5-1000 μm) (see, e.g., U.S. Pat. Nos. 6,824,087 and 6,287,312, the disclosure of each of which is incorporated herein by reference). These devices and other more conventional non-medical milling devices (see, e.g., http://www.alpinehosokawa.com) are adaptable to grinding a tooth into particle size ranges desired for various applications.

An exemplary method of the present disclosure includes combining dental pulp stem cells collected from a tooth of a mammalian donor with native tissue to form a stem cell graft product. This native tissue may comprise tissue from the patient recipient, such as a tooth, or may comprise tissue from the stem cell donor, such as the stem cell donor's tooth. In addition, the patient's own autograft tissues, synthetic tissue substitutes (e.g. SIS, DePuy Orthopedics), or an HLA matched/unmatched allograft may be utilized to expand the quantity of graft material for a particular application. Of course, any of a variety of known methods of making a particulate or structural allograft or autograft may be used with the present disclosure. These include, for example, the methods disclosed in U.S. Pat. Nos. 6,511,509 and 7,018,412, the disclosure of each of which is incorporated herein by reference.

While one may use any human bone in lieu of a tooth for the particulate material according to the present disclosure, there are several potential advantages of using a tooth or teeth as the primary particulate material. Teeth are available for preservation from childhood to teenager providing a very large potential source of THA. Harvesting autograft bone and stems cells from different surgical sites require additional surgery and donor site morbidity (such as inflammation, infection, and chronic pain that occasionally outlasts the pain of the original surgical procedure). As briefly discussed previously, the tooth calcination process creates a sterile product that is non-infectious and that will not illicit a foreign-body reaction in host tissues (HLA typing not necessary once tooth deproteanated). Consequently, the advantages of using bone and/or teeth of the patient include lowering the risk of rejection, abundant supply of stem cells from unerupted teeth, and low to no risk of cancer or other diseases in the stem cells or hard tooth.

In a circumstance where the stem cell donor donated four third molars, and where the matrix/scaffold is not insignificant in size, each of the third molars is preferably ground to provide a greater volume of bone growth slurry to accommodate the larger matrix/scaffold. For example, if four donor third molars are ground, it may provide enough matrix material (including the porosity) for a 3-D cleft palate defect replacement. Alternatively, or in addition, HLA matched or unmatched teeth particulate may be utilized in place of the host ground teeth. Alternatively, or in addition, bone substitutes (HA, TCP, calcium phosphate, etc.) may be used alone or in combination with the host ground teeth to fabricate a larger vertebral body replacement or other bone defect matrix. Moreover, the ground teeth may be used alone or in combination with the native tissue from the stem cell donor, the patient, and/or an HLA matched/unmatched donor to construct the matrix.

Referring back to FIG. 1, in accordance with the instant disclosure, the ground tooth 138 may be combined with the extracted stem cells 136 to create a bone graft slurry 148. Alternatively, the collagen and other soft tissue 134 extracted from the tooth 138 may be combined with the extracted stem cells 136 to create a soft tissue slurry 146. Because of the numbers of stem cells 136 available, it may be that only a portion of the total harvested or cryopreserved cells are needed with the remainder being preserved for later medical use. In general, the larger the applications (such as, multilevel spine fusion in scoliosis) requires more cells, while the smaller usages (such as, injection into a scaphoid non-union) require fewer cells. Also the ratio of stem cells 136 to ground tooth 138 or collagen 134 may vary for example when tooth derived collagen matrix 142 or a ground tooth particulate matrix 144 is to be seeded by immersion (i.e., soaked) in a liquid milieus of cells that diffuse into and attach onto the scaffold porosity 150, 152. For instance, the ratio of stem cells 136 to ground tooth particulate 138 is smaller for injection into a particulate matrix 144 with relatively larger porosity. Likewise, the ratio of stem cells 136 to collagen 134 is smaller for injection into a collagen matrix 142 with relatively larger porosity. Conversely, the ratio of stem cells 136 to ground tooth particulate 138 is greater when the surface of the particulate matrix 144 is grafted to allow for improved graft host junction incorporation or to allow the stem cell slurry 148 to flow into the microporsity or interconnective channels. Similarly, the ratio of stem cells 136 to collagen soft tissue 134 is greater when the surface of the collagen matrix 142 is grafted to allow for improved graft host junction incorporation or to allow the stem slurry 146 to flow into microporosity or interconnective channels. Further, an atrophic non-union may require an increased ratio of stems cells to ground tooth. Nevertheless, the preferred range of ratios of stem cells to ground tooth will depend greatly on the anticipated use and graft needs.

In the same manner, the particulate size required for a particular bone graft slurry 148 varies depending upon application. Similarly, the preferred particle size(s) of the tooth 138 depends in part upon the porosity of the matrix or native host into or onto which the bone graft slurry is applied. Smaller particulate and lower viscosity bone graft slurry 148 and soft tissue graft slurry 146 are needed to penetrate more deeply into the porosity of solid free formed scaffolds 142, 144. However, those applications where it is preferred for the bone graft slurry to stay localized with less containment available generally have a larger particulate size of 500-1,000 µm. A non-union fracture site or filling a larger defect are usages that generally require this larger particulate size. The intermediate sizes of ground tooth, 100-500 µm, are appropriate for a cementless implant ingrowth surface or a scaffold with larger porosity. Autologous and synthetic scaffolding are selected for optimal porosity depending upon the desired application.

As used herein, the matrix 144 into or onto which the bone graft slurry is applied is sometimes referred to as an implant scaffold. The speed of resorption for a bone substitute depends in part upon the presence of interconnected macropores of adequate size (over 100 microns) in the matrix or native host allowing colonization of the implant by osteoclasts and then the resorption or biodegradation.

Figure 2:
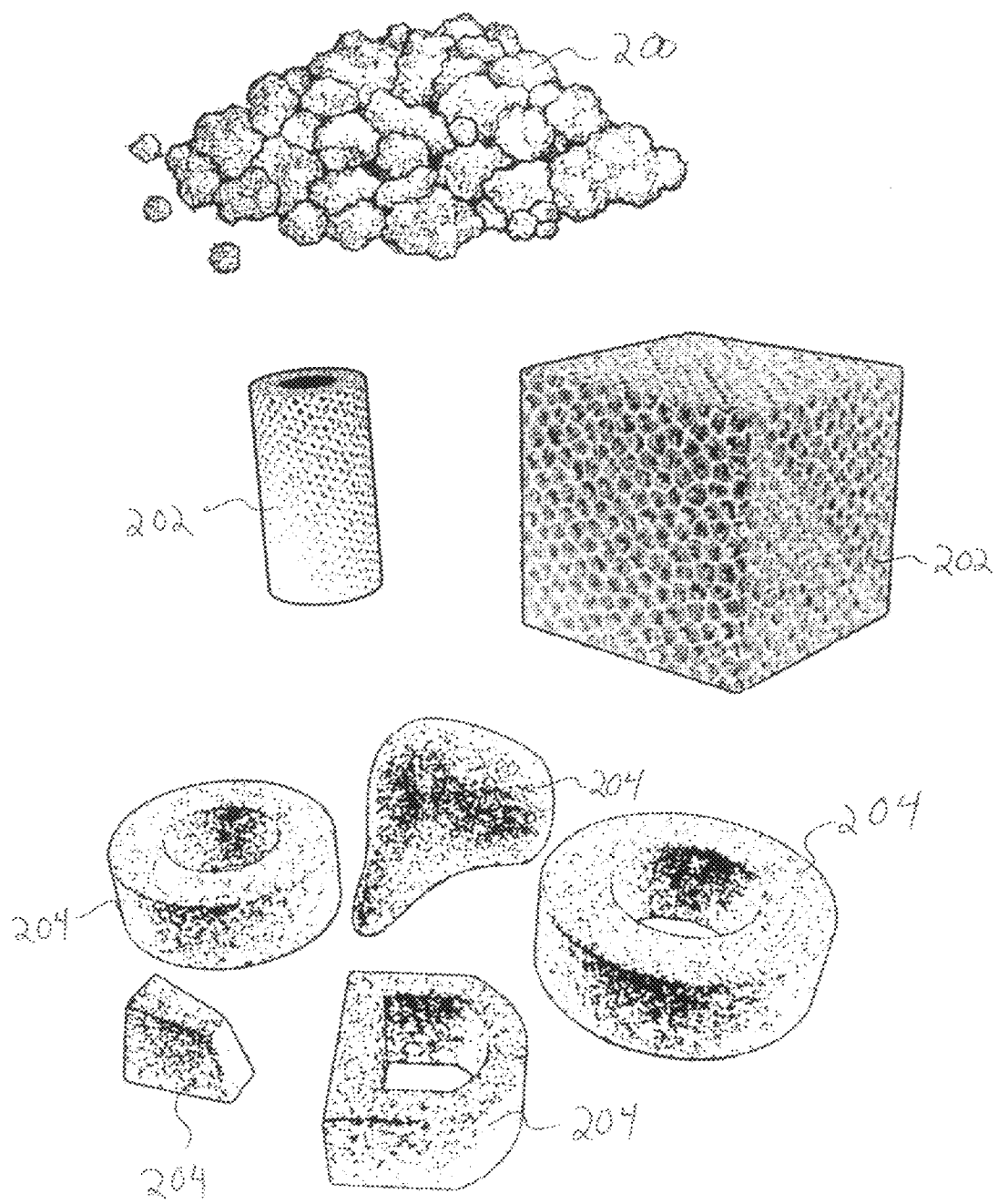
FIG. 2 includes a series of drawings showing tooth hydroxyapatite (THA) graft particulate, a tooth and collagen and soft connective tissue standard shaped scaffolds and matrixes, and various shaped collagen and THA scaffold and matrixes for use with the exemplary embodiments of the instant disclosure.

Referencing FIGS. 1 and 2, THA particles 200 of varying sizes and shapes may also be manufactured from the ground teeth 138. THA particles 200 tend to be larger in size to fill larger graft sites (e.g., acetabular osteolytic defects, segmental bone fragment loss in open fractures, spine fusions, etc.), while smaller in size when filling small defects (e.g., scaphoid non-unions—see FIG. 10). Larger THA particles 200 will also be more frequently utilized in association with open procedures (see, e.g., FIGS. 5, 6, 12C), thereby causing the bone graft 148 to stay more localized. Size and shape in addition to overall porosity percentage and macropore size affect mechanical properties such as compressive strength and crushability. THA particle 200 sizes will vary to meet these graft site mechanical, as well as, biologic demands.

THA particles 200 have certain porosities to promote the desired strength (or crushability) osteointegration and rate of incorporation or resorption. These particles 200 are often characterized by a porosity percent and a size percent of the characteristic macroporosity. A larger matrix/scaffold 144 will also have a greater pore interconnectivity percent (the greater the percent the more likely that resorption, incorporation or revascularization are enhanced). Structural needs often dictate the porosity as increasing porosity usually decreases the structural integrity because porosity is a physical parameter that varies inversely with graft compressive strength. For instance, if mechanical and structural properties of the matrix 144 are similar to those exhibited by GRAFTYS® HBS cement, approximately 65-70 percent total porosity with about 8 percent macroporosity (pores from 100 to 300 microns) would be preferred.

In concert with porosity considerations, the viscosity of the bone graft slurry 148 and soft tissue graft slurry 146 are also important. For example, if the viscosity is too high, the slurry may not adequately penetrate the pores of the scaffold 142, 144. Conversely, if the viscosity is too low, the slurry 146, 148 may prematurely migrate out of the pores of the scaffold 142, 144. If the viscosity of the bone graft slurry 148 or soft tissue graft slurry 146 carrier is too low, a carrier may be used to contain the slurry and scaffold, thereby lessening the impact of viscosity on the bone or soft tissue ingrowth or regeneration.

An exemplary carrier for use with the molar stem cell slurries 146, 148 of the present disclosure is Graftys HBS (www.graftys.com) ("Graftys"). Graftys is a cement material comprising a solid powder phase that initially forms a plastic paste by mixing with a liquid phase. This viscous paste transforms into a stiff paste during setting, with porosity increasing its mechanical strength progressively up to saturation/hardening. In accordance with the instant disclosure, the molar stem cell slurry 146, 148 is optionally applied to a matrix 142, 144 and implanted in contact with a site where bone/soft tissue growth or regrowth is desired. In order to reduce the impact of viscosity on the molar stem cell slurries 146, 148, Graftys may be applied to cover the matrix 142, 144 and bone growth/regrowth site as a cap. Because Graftys hardens into a containment shell relatively quickly, even bone graft slurry with a relatively low viscosity is not a problem. By using Graftys, it is possible to utilize relatively low viscosity slurry 146, 148 to fully penetrate the matrix 142, 144, without the drawbacks of this same low viscosity slurry migrating out of the matrix hours after implantation. But if a carrier or cap is not utilized, additives may be required to change the viscosity of the slurry 146, 148.

Viscosity increasing substances 154 for addition to graft slurries 146, 148 include, without limitation, autogenous blood or blood products (platelet concentrates, plasma concentrates, etc). These substances may take on a dual role to optimize viscosity, while at the same time providing biologic enhancement (growth factors, differentiation, etc). Platelet gels or autologous platelet gels increase the volume of cells used in the graft slurry 146, 148 and also provide initial control of bleeding (hemostasis) and reduce of post-operative bruising. In addition to providing initial control of bleeding (hemostasis) and platelet gels release mediators to help modulate the inflammatory response and many of the cellular functions involved in wound healing. Much of these effects are due to the presence of growth factors and cytokines within the platelets, and the presence of an increased concentration of white blood cells in the gel. Examples of growth factors include platelet derived growth factor, insulin derived growth factor, and transforming growth factor-beta among many others. Growth factors are proteins that impart specific biochemical messages to specific target cells through specific membrane receptors Creation of platelet gels requires harvesting platelet-rich plasma (PRP) from whole blood and combining it with thrombin and calcium or other activators to form a coagulum. The whole blood may be taken from the stem cell patient/recipient or may be take from close relative or HLA matching donor. This coagulum or "platelet gel" is mixed with the bone growth slurry, and possibly with growth factors and white cells, to provide a therapeutic benefit when located in proximity to a surgical wound. As would be expected, addition of the platelet gel to the graft slurry 146, 148 is operative to increase the viscosity of the slurry. In certain circumstances, this may require further addition of a viscosity lowering substance to the graft slurry 146, 148.

Viscosity lowering substances 155 for addition to graft slurries 146, 148 include, without limitation, aqueous components (e.g., sterile water) and solutions thereof that include one or more of the following substances: sodium chloride, potassium chloride, sodium sulfate, potassium sulfate, ethylenediaminetetraacetic acid (EDTA), and phosphate buffered saline solution. By way of example, 0.9% NaCl saline solution, available from Baxter International (www.baxter.com), may be added to the graft slurry 146, 148 to reduce its viscosity.

While viscosity is an important consideration, other considerations may give rise to incorporating other additives, such as antibacterial or antifungal additives 157, into the graft slurries 146, 148 and/or matrix/scaffold 142, 144 to discourage infection at the tissue growth/regrowth location. The type and amounts of these additives 157 will vary depending upon the potential pathogen (is often site dependent) and the relative toxicity to the stem cells or bone inhibition effects. These additives 157 include standard antibiotic medicines and antimicrobial compositions such as, without limitation, penicillin and metal alloys of copper and silver. These additives 157 also include standard antifungal medicines, including, without limitation, econazole, fenticonazole, miconazole, sulconazole, tioconazole, amphotericin, nystatin, terbinafine, itraconazole, fluconazole, ketoconazole, and griselfulvin. In certain instances, antifungal medicines are combined with other medicines when two actions are desired. For example, an antifungal medicine is often combined with a mild steroid, such as hydrocortisone, to treat fungal infections with concomitant inflammation.

Additional additives 159 may be combined with (or incorporated into) the tissue graft slurry 146, 148 and/or matrix/scaffold 142, 144 such as graft incorporation enhancing medicines and bone or collagen antiresorptive medicines. Bone-graft materials usually include one or more components: an osteoconductive matrix, which supports the creation or ingrowth of new bone; osteoinductive proteins, which support mitogenesis of undifferentiated cells; and osteogenic cells (osteoblasts or osteoblast precursors), which are capable of forming bone in the proper environment. The bone graft slurry 148 will provide the needed osteoinductive mineral via ground tooth 138, while the stem cells 136 will provide the osteogenic progenitor cells. The combination and simultaneous activity of many potential additives results in the controlled production and resorption of bone. These factors (residing in the normal extracellular matrix of bone) include TGF-beta, insulin like growth factors I and II, PDGF, FGF, and BMPs.

Using current techniques, in vitro differentiation of mesenchymal stem cells toward the osteoblast lineage is possible. Stem cells are cultured in the presence of various additives such as dexamethasone, ascorbic acid, and b-glycerophosphate to direct the undifferentiated cell toward the osteoblast lineage (see U.S. Patent App. Publication No. 2009/0155216, which is incorporated herein by reference). The addition of TGF-beta and BMP-2, BMP-4, and BMP-7 to the culture media also influence the stem cells toward the osteogenic lineage. For example, marrow cells containing mesenchymal stem cells may be combined with porous ceramics and implanted into segmental defects, with bony growth occurring as quickly as 2 months. Mesenchymal stem cells can also be seeded onto bioactive ceramics. Factor-based bone graft substitutes have been isolated and synthesized, used alone or in combination with other materials such as transforming growth factor-beta (TGF-beta), platelet-derived growth factor (PDGF), fibroblast growth factor (FGF), and bone morphogenetic protein (BMP). The type and amounts of these osteogenic enhancing/differentiating factors will vary depending upon the site dependent needs.

Anti-resorptive medicines that slow or stop the natural process that dissolves bone tissue, resulting in maintained bone density and strength may also be utilized in combination with the graft slurries 146, 148 of the instant disclosure. In circumstances where bone loss or density is a concern, antiresorptive medicines are operative to prevent or retard further development of osteoporosis. Exemplary anti-resorptive medicines include, without limitation, bisphosphonates. Some examples of bisphosphonates include alendronate, etidronate, ibandronate, risedronate, and zolendronic acid. Exemplary methods of coating an implant device with bisphosphonates are disclosed in U.S. Patent Publication No. 20060188542 and U.S. Pat. No. 7,163,690, the disclosure of each of which is incorporated herein by reference.

Autologous and Allograft Procedures

By way of example, and not limitation, the exemplary techniques and formulations of the present disclosure are useful in primary pediatric orthopedic procedures including spine fusion and other joint fusions such as ankle fusions for club feet treatment and fractures high non-union rates such as scaphoid and distal third tibial fractures. Additionally, by way of example and not limitation, exemplary primary pediatric orthopedic procedures that can benefit from these products and methods include, limb lengthening procedures, atrophic fracture non-unions, and fractures with high non-union rates such as distal tibia fractures, scaphoid fractures, fifth metatarsal fractures, femoral neck fractures and clavicle fractures. Pediatric cases are ideally suited as they may have molars available for harvest at the time of surgical need. Adult orthopedic uses mirror most of the above but also include cementless total joint replacement surgery, and other orthopedic bony, tendon and ligamentous conditions having a relatively high incidence of failure using prior art techniques and compositions of matter.

Spinal Fusion Example

Figures 4, 5:
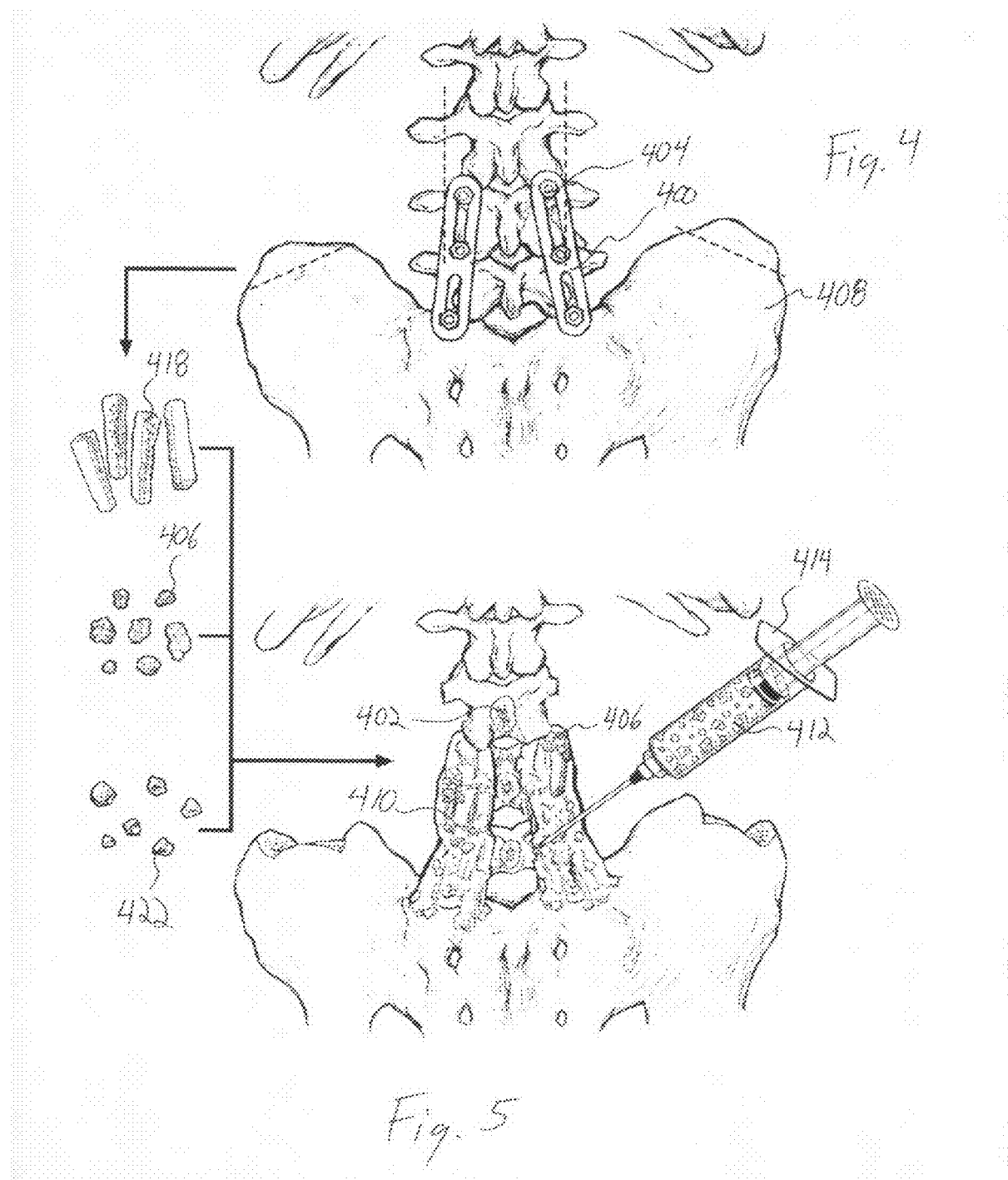
FIG. 4 is a rear view of a human spinal fusion device showing the spinal fusion bracket instrumentation in position.
FIG. 5 is a rear view of a human spinal fusion making use of a stem cell molar graft bone slurry located proximate the intended bone fusion locations.

Referring to FIGS. 1, 4 and 5, an exemplary procedure in the context of primary pediatric orthopedic procedures includes a spinal fusion. Such a procedure necessarily involves harvesting dental pulp and isolating autologous stem cells from an appropriate donor, whether from the patient himself or an HLA matched relative. The harvesting may be done immediately prior to the spinal fusion procedure under the same anesthetic or may be carried out well prior to the fusion procedure presuming some sort of preservation technique is utilized for the stem cells, such as, without limitation, cryogenic preservation. In any event, it is preferred that within 72 hours of the primary pediatric orthopedic procedure, in this case a spinal fusion, the dental pulp stem cells 136 are combined with ground tooth particulate 138 to create a stem cell molar graft slurry 148 for use in a pediatric spinal fusion procedure.

By way of example, a pediatric spinal fusion procedure may be carried out to correct deformities associated with scoliosis. Scoliosis spinal fusions are generally carried out using one of two approaches. A first approach is a posterior spinal fusion where a vertical incision in the posterior of the patient is made, proximate the spine, while the patient is lying on his/her stomach to expose the vertebrae. A second approach includes making incisions on the lateral side of the patient, while the patient is lying on his/her second lateral side, to access the spinal column. During this second procedure, the patient's lung is deflated and a rib removed in order to reach the spine.

During surgery (either or both surgical exposures), after the spine is exposed, the surgeon attaches a metal plate 400 to each side of the patient's spine 402 using hooks or screws 404 that are most commonly attached to the vertebral bodies as is commonly known to those skilled in the art. Sublaminar wires (not shown) and screw fixation are utilized at the multiple levels to be fused. The metal plates 400 attached to the spine ensure that the spine remains straight and rigid while the spinal fusion takes place.

Molar graft bone particles 406 can be added if available from autologous or allogenous sources. Autologous harvested bone graft 418 (from the bone removed from the spine 402 and iliac crest 408) is ground and thereafter added to the fusion mass along with the stem cell bone graft slurry 412. The bone graft slurry 412 is injected, using a syringe 414, proximate locations where bone fusion is preferred. In addition, THA particles other bone graft extenders 422 and autologous (e.g., platelet gels) and allogenous or synthetic (e.g., BMP) growth factors may be applied as determined by the surgeon. The entire length of the deformity is generally grafted (anywhere up to 15 levels between T3-L5), but in this exemplary depiction only the L3-L5 vertebrae being fused.

By way of example, prior to injecting the bone graft slurry 412, a platelet gel is prepared by harvesting sixty cc's (two ounces) of the patient's blood just prior to surgery. The blood is placed into a specially designed tube, which is centrifuged for about 15 minutes. This centrifuge process concentrates up to 80% of the natural healing factors that are in the blood. The platelet concentrate is placed sterily on the surgical field in a 10 cc syringe (not shown). This is paired with a 1 cc syringe of calcium and purified bovine thrombin in a double-barreled syringe, much like an Epoxy gun (not shown). The contents of the syringes are mixed when the products are sprayed into the wound to create a sprayed platelet gel.

Thereafter, the stem cell molar graft slurry 412 is applied using the syringe 414 to deposit slurry droplets throughout the fusion levels, with particular attention likely given to the proximal and distal fusion junctions where non-union rates are the greatest. The bone graft slurry 412 facilitates bone growth and fusion of the vertebrae segments (in this case L3-L5) as the fixation plates 400 and screws 404 temporarily stabilize the spine 402. The patient is often braced to promote further spinal fusion healing by decreasing the likelihood of segmental motion between the vertebral segments holding them immobile and straight. After injecting the molar graft slurry 412, the perispinal and fascial closure (not shown) operate to hold the molar graft slurry 412 contained in the regions where fusion is needed.

In this example, the molar graft slurry 412 comprises approximately 5 cc's of slurry with a drop or two being placed at each level where fusion is desired. The volume of the molar graft slurry 412 may be greater if mixed with blood, platelet concentrate, and/or serum 154. Exemplary needle gauges for use in injecting the exemplary molar graft slurry 412 include, without limitation, 12 gauge to 21 gauge.

In circumstances where the fusion site is closed with soft tissue, the molar graft slurry 412 can be injected after initial grafting and final wound closure. Hemostasis to prevent the molar graft slurry extravasation can be obtained by packing a combination of Gelfoam (available from Upjohn, of Kalamazoo, Mich.) and thrombin, or bone wax can be applied to the raw osseous surfaces to stop the bleeding. Packing with lap sponges also helps to control the bleeding. The stem cell molar graft slurry may also be injected into the site at the end of the procedure (necessarily a less viscous slurry with smaller particulate size) when a layered closure is utilized in order to insure containment of the slurry. Autograft or allograft ligament or synthetic soft tissue closure materials (e.g., Small Intestinal Submucosa RESTORE Orthobiologic Soft Tissue Implant, available from DePuy Orthopedics, Inc.) may also be used to help create a containment compartment for the molar graft slurry 412 to prevent its extravasation and possible stimulation of heterotopic bone formation.

In this example, the particulate size has a bimodal distribution varying between 5-100 µm for injection. However, it should be understood that particle sized outside of this range may be used in accordance with the instant disclosure. As discussed above, the molar graft slurry 412 may include blood or a generic platelet gel (e.g., DePuy Biologics SYMPHONY™ II Platelet Concentrate System) or other aqueous solutions to obtain the appropriate viscosity. It should be understood that the ratio of the different component amounts (e.g., stem cells, ground tooth, and other optional components) correspondingly affects the viscosity of the slurry. Depending on whether the graft is to be applied to the fusion site alone, or in conjunction with expanders, also affects ratio of the various components of the molar graft slurry 412. Larger ground tooth particulate 406 sizes and more viscous solutions, like platelet concentrates, generally work better when the molar graft slurry 412 is applied directly into the fusion site (with or without other autograft, allograft, synthetic materials and expanders). Moreover, the graft site may be sealed to contain the molar graft slurry 412 by using sealing products that harden such as, without limitation, Graftys HBS (www.graftys.com).

Alternatively, or in addition, the molar graft slurry 412 may be injected at postoperative intervals to facilitate spinal fusion, most commonly at the proximal and distal fusion points, particularly when radiographic evidence of fusion is lacking. By way of example, postoperative injections may be delayed hours or days after homeostasis and swelling have stabilized. In cases where fusion failure is suspected, particularly at the critical proximal and distal fusion segments, a molar graft slurry 412 with a higher stem cell to THA ratio would most often be used.

The foregoing procedure may be adapted to treat other joint fusion procedures at index procedure, or postoperatively to augment or treat a failed or failing fusion due to poor biologic conditions inherent to certain cases (e.g., cervical fusions (interbody and lamina), subtalar and tibiotalar arthrodeses, metacarpal wrist carpal arthrodeses). Introduction of a molar graft slurry 412 in accordance with the instant disclosure addresses both the biological and the mineral content considerations for optimal bone growth.

Bony Non-Unions Example (And Fractures with High Non-Union Rates)

Referencing FIGS. 6-11, another exemplary orthopedic procedure for which bone graft slurries in accordance with the instant disclosure may be utilized involves bony non-unions that are atrophic or hypotrophic resulting from fractures that fail to unite due to poor biologic conditions. Certain fractures have very high rates of not healing such as, without limitation, cervical, distal tibial diaphyseal fractures, clavicle fractures, femoral neck fractures, scaphoid, fifth metatarsal fractures.

Referring to FIGS. 9-11, an exemplary fracture with a high non-union rate is the scaphoid fracture of the wrist 900. In the undisplaced fracture, a stem cell molar graft slurry 902 formulated in accordance with the instant disclosure is injected by fluoroscopic guidance into the fracture zone 904 using a syringe 906. The stem cell molar graft slurry 902 is contained within the fracture hematoma or contained by the surrounding carpal ligaments and soft tissue 908. An external fixator, cast or brace (not shown) may also be used to hold the wrist carpal bone stable to limit motion and promote fracture healing. Normally, 3-6 month of cast or fixator immobilization is required for healing. Increased rate of healing or decreased rate of fracture non-union are extremely valuable from a cost and patient morbidity perspective. In a similar closed percutaneous fashion, other non-displaced fractures known to have high non-union rates may be similarly treated. In addition, growth factors and other healing agents may be added or formulated by the surgeon as needed to create a stem cell molar graft slurry 902 promoting successful or expedited healing.

When open reduction and internal fixation is required for the displaced scaphoid fractures, a Herbert Screw 910 is often used for fracture fragment fixation and stabilization. Stem cell molar graft slurry 902 is added to the open fracture zone 904 with additional molar particle graft or autograft, as necessary. Drops of low viscosity stem cell molar graft slurry 902 with small THA particulate are added and operative to penetrate the fracture zone 904 (see FIG. 10). Conversely, a more viscous stem cell molar graft slurry 902 may be used for fractures evidencing greater bone particulate (evidence of the bone being crushed) or bone loss at the fracture zone 904. The soft tissues 908 surrounding the fracture zone 904 are closed over the region to contain the stem cell molar graft slurry 902. Growth factors or other bone healing adjuncts may be added to further promote successful healing over a shortened period of time. Those skilled in the art will understand that various external fixation adjuncts may be used to retain the bones in alignment such as, without limitation, external braces.

An exemplary stem cell molar graft slurry 902 is fabricated in accordance with the instant disclosure. For a young child or teenager patient, unerupted wisdom teeth (such as tooth 1732 in FIG. 17) may be extracted and thereafter the pulp from the pulp chamber 120 (where the stem cells are located) is separated from the dentin and the tooth enamel from the crown 110 (see FIG. 1). Depending upon the duration between tooth extraction and the surgical procedure to repair the bony non-union, the stem cells are preserved using either short term or long term preservation techniques. In exemplary form, for a young child or teenager, one or more unerupted molars are extracted, the pulp is separated from the remainder of the tooth mass, and just prior to the time of injection, the stem cell molar graft slurry 902 is prepared on a sterile side table. Alternatively, if the molar stem cells were previously cryopreserved, the stem cells are unfrozen the day of the surgery and combined with ground tooth to form the stem cell molar graft slurry 902. For application in bony non-unions, the bone graft slurry is formulated to embody a more viscous consistency.

Figures 6, 7, 8:
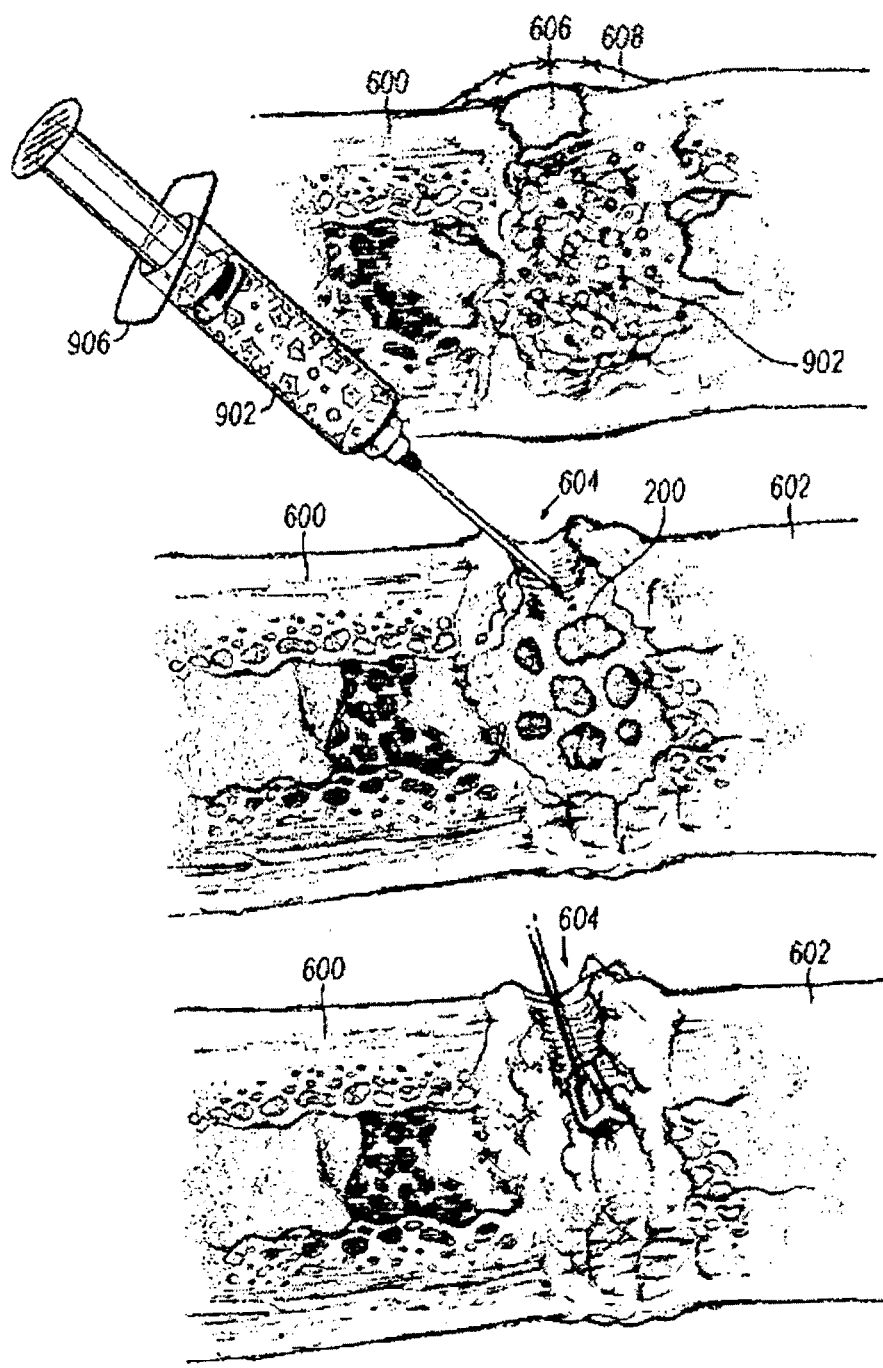
FIGS. 6-8 include a series of figures showing human bony non-unions and how the non-unions are treated with stem cell molar bone graft slurry and THA, and thereafter enclosed, to facilitate bone formation at the non-union site.
Figure 8:
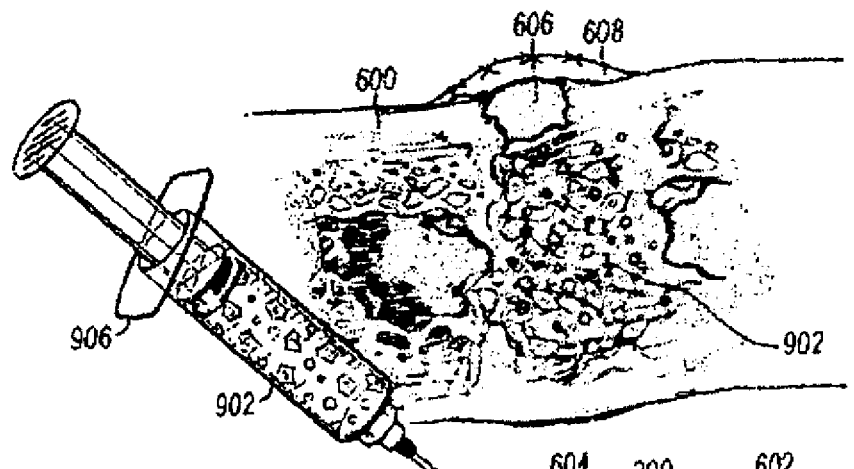
Figure 7:
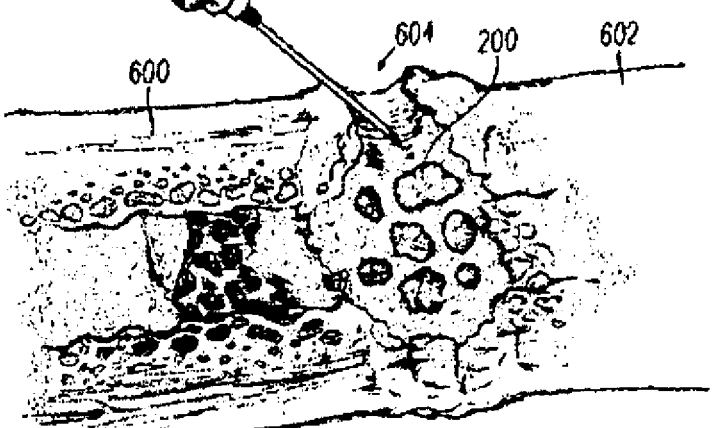
Figure 6:
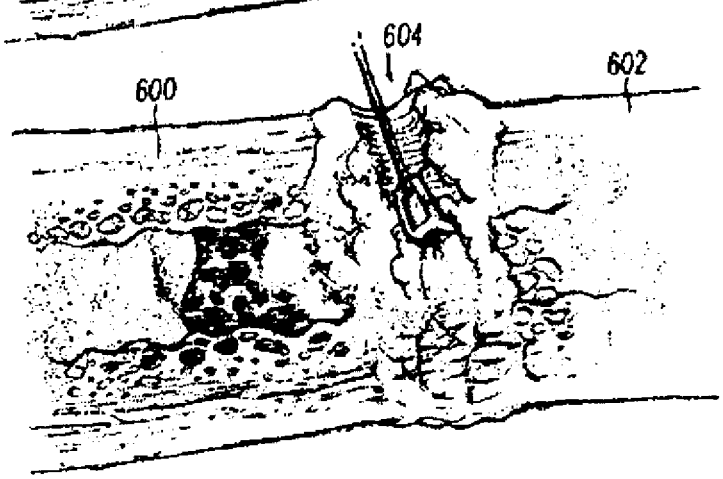

Referring to FIGS. 6-8, an exemplary surgical procedure to repair a bony non-union between a first bone section 600 and a second bone section 602 includes surgically excising and curettaging to create a cavity 604 at the non-union location, with both bone sections 600, 602 providing good surrounding bleeding bone. The cavity 604 is then grafted with autograft or HLA matched stem cell molar graft slurry 902. The stem cell molar graft slurry 902 may or may not include additional patient autograft (such as patient THA particles 200 shown in FIG. 2) or synthetic bone mineral extenders, biologic graft, and autologous patient growth factors. Those skilled in the art, particularly surgeons, will understand which aspects to mix based upon one or more of the following: the foregoing disclosure; real-time considerations in the operating room; patient-specific considerations; and, innate knowledge. The formulated stem cell molar graft slurry 902 is thereafter injected into the cavity 604 using a syringe 906 to substantially fill the cavity. The top of the cavity 604 is then closed with a sealant or cap 606 (e.g. Grafty's). In addition, soft tissue 608, such as periostium or fascial layers, also offer options of deep coverage and containment of the stem cell molar graft slurry 902. Moreover, the stem cell molar graft slurry 902 may be cryopreserved and injected into the non-union location days or weeks after the initial non-union surgical procedure.

The non-union location can alternatively be minimally exposed through a limited incision in order to create entry into the fibrous scar tissue. The stem cell molar graft slurry 902 is then injected at the location of the non-union to promote continued bone ingrowth and healing. The surrounding fibrous non-union tissues are operative to maintain the slurry 902 in position. Nevertheless, the slurry 902 maintains is position also by use of external stabilization, such as an external fixator or brace, that is operative to limit bone fracture non-union motion, thereby enhancing healing.

In another exemplary form, the stem cell molar graft slurry 902 is injected percutaneously (without open incision) using needle guidance techniques, directly into fractured areas without direct exposure of the fractured areas. This is of particular benefit in the treatment of vertebral compression fractures in combination with or without vertebral body expansion technologies. This conservative closed treatment prevents a myriad of complications that occur after attempted open treatment (that further devascularize these fractures). The same holds true for using the stem cell molar graft slurry 902 for fracture grafting in cases of delayed healing or significant initial bone loss.

Referring to FIG. 12, an exemplary application in accordance with the instant disclosure is the formation of vertebral bone for the orthopedic treatment of vertebral fractures in osteoporotic patients or the injection of the bone molar graft slurry into an osteoporotic vertebral body pre-fracture. Recent assessments place the number of annual vertebral fractures to exceed over 700,000 cases. Pursuant to the instant disclosure, vertebral bone formation may be accomplished in multiple ways including, without limitation, in vitro bone formation and in vivo bone formation.

An exemplary percutaneous treatment of a vertebral fracture of a vertebral body 1200 includes approaching the vertebral body through the pedicle 1202 to provide a conduit for a stem cell molar graft slurry formulation 1204 to be injected, using a syringe 1206, into a defect or fracture zone 1208. In this exemplary application, the stem cell molar graft slurry 1204 is formulated to include THA combined with autologous harvested bone or synthetic graft materials that are operative to increase the mineral content of the slurry. In patients with harbor bone a minimally invasive incision is made down to the vertebral body pedicle 1212 and a corresponding hole 1210 created in the vertebral body through which the stem cell molar graft slurry 1204 is injected and then sealed off using Floseal or another similar hemostatic agent. In the alternative, the hole 1210 may be filled using a bone or synthetic plug (not shown).

In vivo vertebral body replacement may also be accomplished using an artificial shaped or natural matrix/scaffold (not shown) in the shape of the vertebral bone to be replaced. The matrix/scaffold is formed in-vitro with the desired porosity is utilized as a chassis for bone formation. In exemplary form, the shaped matrix/scaffold may comprise, without limitation, one or more of the following: collagen, demineralized bone, tricalcium phosphate, hydroxyapatite, coralline hydroxyapatite, calcium sulfate, bioactive glass ($SiO_2$) and carbonated apatite (e.g., OsteoGraft [DENTSPLY Friadent CeraMed, Lakewood, Colo.], Norian SRS [Synthes, Inc, West Chester, Pa.], ProOsteon [Interpore Cross International, Irvine, Calif.], Osteoset [Wright Medical Technology, Inc, Arlington, Tenn.]). After the matrix/scaffold formed, it is subsequently embedded with stem cell molar graft slurry comprising a mixture of stem cells and tooth particulate as previously described herein. In order to thoroughly embed the stem cell molar graft slurry within the matrix/scaffold, soaking and/or vacuum infusion may be carried out on the matrix/scaffold. Either or both of these techniques may be carried out in an operating room just prior to implantation of the matrix/scaffold. One skilled in the art is knowledgeable as to the plethora of ways a graft slurry may be applied to a matrix/scaffold to introduce the stem cells and ground tooth into the microporosity. In like part, the viscosity of the slurry will in large part depend (or at least should depend) upon the porosity of the matrix/scaffold to which the stem cell molar graft slurry is to be applied. As discussed previously, larger porosity can accommodate relatively higher viscosity slurries, whereas smaller porosity should be matched with lower viscosity slurries. In any event, the stem cell molar graft slurry is operative to promote incorporation and revascularization.

In the case of pending pathologic fractures or severely osteoporotic patient (see FIG. 12D), injection of the stem cell molar graft slurry takes place in a non-operative setting. By way of example, after a radiation procedure is carried out for a pathologic fracture, the stem cell molar graft slurry is injected proximate the pending fracture in the operative setting. Metastatic fractures or pending pathologic fractures before or after irradiation pose a great problem for orthopedic surgeons. The instant stem cell molar graft slurries provide a solution to these previously unsolved circumstances because the slurry provides both the biology (molar stem cells) and the mineral content (THA) to facilitate bone reformation. In addition, chemotherapeutic agents, antibiotics as well as additional bone healing agents and growth factors could be added to the slurry.

In exemplary form, the pending fracture comprises a metastatic osseous lesion. By using fluoroscopic guidance as shown in FIG. 12D, the stem cell graft slurry is injected precisely into the proper location to stimulate bone growth potential in one or more areas where radiation has previously eviscerated native bone growth potential. Alternatively, after minimal pathologic lesion curettage and debridement, the stem cell molar graft slurry can be injected and accordingly covered and contained.

Limb Lengthening Example

In in vivo bone formation, in contrast to in vitro bone formation, the natural bone of the patient may be fractured, non-united, or include some other bone cavity into which bone formation is preferred. In this circumstance, a bone cavity or bone defect already exists or is enlarged to receive bone graft slurry formulated in accordance within the instant disclosure. Preparation of the bone cavity may include reaming and surgical placement of screws or other fastening devices to maintain the residual bone(s) in position so that subsequent bone formation is operative to at least partially fill the cavity. In addition to receiving the bone graft slurry, the bone cavity may receive a natural or artificial matrix/scaffold. An example where in vivo bone formation is necessary for success is limb lengthening procedures.

Referring to FIG. 13, exemplary Ilizarov and/or limb lengthening or reshaping procedures (e.g., distraction osteogenesis) benefit from infusion of a stem cell molar graft slurry 1300 formulated in accordance with the instant disclosure. By way of background, limb lengthening or reshaping procedures involve osteotomy and periodically (i.e., daily) stretching the bone slowly so that bone formation occurs between the bone gaps caused by the fracture as a means to increase the overall length of the bone. In the case of a patient with a leg length discrepancy, for example, due to the tibia and fibula bones in one leg being shorter than the other, an osteo-distraction surgical procedure begins by mounting an external Ilizarov fixation device 1302 to the proximal and distal ends of the tibia 1304 and fibula 1306 with respect to the locations 1308 where the intercalary osteotomy is to be done. Thereafter, the bone cortex is circumferentially cut via a minimal incision with the rigid fixation device preventing displacement of the bones 1304, 1306.

At open surgical exposure, a high viscous stem cell molar graft slurry 1300 is prepared in accordance with the present disclosure and is injected at the time of the osteotomy into the canals of the bones 1304, 1306, proximate the fracture, to promote an initial patient osteogenesis response. The slurry 1300, if mixed well in advance of the Ilizarov fixation device mounting procedure, is preferably stored at a low temperature to avoid stem cell viability loss. If very small osteotomy incisions are utilized, then the slurry 1300 can be injected using a syringe 1310 through the osteotomy incisions and into the locations 1308 where the bones 1304, 1306 were fractured. In order to ensure that the stem cell molar graft slurry 1300 is retained proximate the fracture, coagulated blood, waxes, absorbable gelatins (such as Gelfoam, and the compositions disclosed in U.S. Pat. No. 6,863,900, the disclosure of which is incorporated herein by reference), clotting agents, and/or sealants (e.g., platelet gel) may be utilized to cap or seal off the slurry, thereby maintaining it in location of the osteotomy.

By using the stem cell molar graft slurry, it is possible to increase the rate of lengthening of the bone because the slurry provides the building blocks for more rapid bone formation. At the same time, using the stem cell molar graft slurry decreases the incidence of needing to stop bone lengthening as a result of poor healing at the fracture site.

After osteotomizing the bone, the body begins to repair the fracture by ingrowth of bone into the gap created by the fracture. This bone regrowth occurs as the result of the patients' own bone healing factors and neo-vascularity entering the osteotomized region in combination with the stem cell molar graft slurry 1300. Over time, the external fixation device is adjusted to incrementally increase the spacing between portions of the fixation device mounted to opposite sides of the bone fracture rings attached to the fractured bones 1304, 1306. This adjustment causes the fractured bone ends to be slowly pulled in opposite directions from the osteotomy site to gradually lengthen the bones (in this case, a tibia and fibula) to the desired length. Depending upon the extent of bone regrowth, five or more adjustments may be made in a 24-hour period to increase the bone length by one millimeter or more. Over time, the incremental distractions result in a considerable lengthening of the limb over time.

Alternatively, or in addition, after a predetermined duration post osteotomy as the lengthening procedure continues to be carried out days, and possibly weeks, from the initial Ilizarov fixation device mounting procedure, a less viscous slurry 1300 (i.e., a slurry having higher stem cell to particulate ratio as compared to the slurry prepared and applied during the Ilizarov fixation device mounting procedure) is injected through the soft tissue down to the osteotomy locations 1308 so that the deep soft tissues, clot, and scar surrounding the bone regrowth locations 1308 are operative to contain the slurry. This less viscous slurry 1300 may be injected on a single occasion or on multiple occasions proximate the osteotomy site. The additional influx of pluripotent stem cells and bone graft material is operative to infuse cells and compatible biologic materials that rapidly transform into bone tissue more rapidly than the natural human body is capable of. In circumstances of failing distraction or when more rapid to distraction is desired, the stem cell molar graft slurry 1300 is formulated to include even higher ratios of stem cells to THA (with or without bone-enhancing additives).

Those skilled in the art, in view of the instant disclosure, will realize that the less viscous stem cell molar graft slurries 1300 may be combined with growth factors where the expanding bone is not highly vascularized. Likewise, these growth factors may be injected separate from the molar graft slurry 1300 proximate the bone formation locations.

Cementless Total Knee and Other Partial and Total Joint Arthroplasty Example

Referring to FIGS. 14-16, those skilled in the art are familiar with total knee arthroplasty (TKA) procedures. In such a procedure, the proximal end of the tibia 1400 is resurfaced to receive a prosthetic tibial insert 1402 (commonly identified as a tibial tray) and the distal end of the femur (not shown) is resurfaced to receive a prosthetic femoral component 1404 (commonly identified as a femoral condylar replacement). Likewise, the patella may also be resurfaced to receive a cementless patellar component 1412. In exemplary form, the prosthetic tibial insert 1402 regularly includes a stem 1406 that is inserted into the tibial intramedullary canal and may be retained within the intramedullary canal using a cement to concurrently bonding to the tibial insert 1402 to the tibia 1400. Alternatively, prosthetic tibial inserts 1402 have been marketed with a stem 1406 having a porous or micro-porous surface adapted to allow bone ingrowth so the stem is mounted directly to the tibia 1400 without cement. Likewise, some prosthetic femoral components 1404 include an interior surface (which is adjacent to the femur when implanted) that is porous and adapted to allow bone ingrowth, thereby mounting the femur to the femoral component 1404.

It has been found in recent years that bone ingrowth into porous surfaces of these prosthetic components 1402, 1404, 1412 does not occur sufficiently to retain the components in proper orientation, thereby requiring revision surgeries to cement the components in a permanent position. But stem cell molar graft slurries 1408 formulated pursuant to the instant disclosure offer a solution for insufficient bone ingrowth, thereby obviating cementing prosthetic components and revisions surgeries inherent with cemented prosthetic components.

In exemplar form, a stem cell molar graft slurry 1408 in accordance with the instant disclosure is created. Because many recipients of joint replacement components, in this case, knee replacement components, are older and no longer have teeth from which stem cells may be gathered, the instant disclosure nonetheless provides an alternative for these patients. HLA allogenic matching can be utilized to obtain molar stem cells stored by a cryogenic bank or storage facility. However, blood-related family members of the patient may have teeth yet to be removed from which stem cells can be harvested or these same family members may have stem cells from their teeth already harvested and in cryopreservation. By using stem cells from close blood-related family members, the risks associated with an adverse immune reaction are significantly reduced.

As previously mentioned, it is not just the harvested molar stem cells that are important, but also making use of the tooth/teeth as a bone graft material in conjunction with these stem cells. That being said, autograft extenders from the patient undergoing the arthroplasty procedure reduce the amount of donor tooth material necessary (say, one or two molar teeth) to fabricate an appropriate stem cell molar graft slurry 1408. The preferred autograft extender that is readily available in most arthroplasty procedures is the finely morselizing bone from the patient resected joint surfaces which is removed as a normal part of the arthroplasty procedure. An exemplary aspect of the stem cell molar graft slurry 1408 is more highly concentrated with stem cells than THA because morselizing bone from the patient can supply most of the hydroxyapatite needed, thereby preserving donor THA for later autologous needs.

In exemplary form, a typical TKA procedure is carried out to reshape the surfaces of the distal tibia 1400 and proximal femur to receive the tibial and femoral components 1402, 1404, which results in removal of some of the tibia and femur. Those skilled in the art are familiar with the initial incisions and resurfacing necessary to prepare the tibia 1400 and femur for the prosthetic components 1402, 1404 and accordingly, only for purposes to promote brevity, those aspects are not explained in detail. As discussed directly above, some of the bone removed from the femur and tibia 1400 is retained (not discarded) in order to function as an autograft extender. When the tibia and femur are resurfaced and ready to receive the cementless prosthetic tibial insert 1402 and femoral component 1404, the resurfaced areas of the femur and tibia, as well as the tibial intercondylar channel, are coated with the stem cell molar graft slurry 1408 using a syringe 1410 or by hand. Moreover, the slurry 1408 may be manually applied using a spreader or may be sprayed onto the tibia 1400 and femur prior to mounting of the prosthetic implants. Alternatively, or in addition, the stem cell molar graft slurry 1408 may be applied to the porous bone ingrowth surfaces of the prosthetic implants 1402, 1404 to promote and accelerate bone ingrowth into the porous surfaces of the implants. When applied to the prosthetic implants 1402, 1404, the stem cell molar graft slurry 1408 is applied to coat the ingrowth surface at the time just prior to final impaction. It should be understood, however, that the slurry 1408 need not be 100% uniform or completely covering all of the resurfaced areas to the tibia 1400 and femur, the porous surfaces of the implants 1402, 1404, or the intercondylar channel.

The press fit impaction, along with limited weight bearing or joint motion for a predetermined period of time, is operative to hold the prosthetic components 1402, 1404 stable to with respect to the tibia and femur to allow for enhanced integration and accelerated bone ingrowth. For TKA, this predetermined period of time when limited weight bearing and joint motion is permitted is not so long as to be detrimental to the final range of motion of the prosthetic joint. No longer than two weeks of restricted joint motion and weight bearing should be necessary.

It should be understood that the foregoing exemplary procedure is equally applicable to fixed and mobile bearing knee joint implants, as well as posterior cruciate retaining knee implants with significant cam-to-post interaction. Also, the molar graft methods and products described herein for TKA could be used to enhance fixation of any partial or total ingrowth arthroplasty including but not limited to hip replacement, shoulder replacement, ankle replacement, elbow replacement, and disk and vertebral body replacement.

Reconstructive Plastic Surgery Example

In reconstructive plastic surgery, the surgeon is tasked with finding a man-made solution to significantly distorted physical features in an attempt to reduce the distortion and, in some cases, approximate a natural appearance. These significantly distorted physical features may be the result of genetic defects, illness, or physical injury (such as an automobile accident or post surgical procedure). The exemplary stem cell molar graft slurries of the instant invention are useful in plastic surgery to repair these distorted physical features.

An exemplary reconstructive plastic surgical procedure where stem cell molar graft slurries includes reconstructive surgery to repair bones after tumor removal that has left a defect of a specific shape in the bone. In a circumstance where a small 3-D defect is present and a 3-D custom scaffold is necessary to improve the cosmetic result, a solid free form (SFF) scaffold may be fabricated using CAD/CAM methodologies to create the requisite 3-D shapes from ground tooth particulate. Exemplary techniques to fabricate the matrices include, without limitation; selective laser sintering and 3-D printing. Both of the foregoing process involve thermal temperatures operative to destroy living cells, however, as has been discussed previously, the matrix/scaffold formation occurs prior to introduction of the stem cell molar graft slurry. However, after arising technology may allow for layering methods may allow scaffolds to be incrementally built up from prefabricated thin (0.25 mm-1 mm) layers, stacked upon one another to form the final 3-D structure that provide an opportunity for incrementally seeding each layer with the stem cell molar graft slurry, rather than an immersion technique for cells intercalation. In any event, the 3-D matrices have porosity characteristics tailored to the end application, which involves stem cell molar graft slurries of varying viscosities depending upon the intended use.

As discussed previously, formulation of the stem cell molar graft slurry includes utilizing stem cells extracted or derived from teeth. The viscosity of this resultant slurry may be impacted by adding autogenous blood or blood products such as platelet jells to increase the viscosity, or aqueous solutions to decrease the viscosity. For example, the same bone graft slurry may be divided to create two distinct slurries one with a relatively high viscosity, and one with a relatively low viscosity for use with reconstructive surgeries.

By way of example, the customized 3-D matrix is soaked in the appropriate viscosity and particulate sized stem cell molar graft slurry. The particles of THA are chosen or ground to be smaller than the matrix pore size to allow the needed penetration into the 3-D matrix. Alternatively, or in addition, other custom or non-custom THA or synthetic scaffolds may be used. Each addition matrix is preferably soaked or coated in a stem cell molar graft slurry of the appropriate viscosity.

During the reconstructive surgical procedure, the bone(s) subject to revision is targeted and one or more bone sections or portions are removed to eliminate or reduce the deformity. Thereafter, the 3-D matrix (loaded with the stem cell molar graft slurry) is attached to the ends or exposed portions of the bone that remain and is affixed using known fixation methods. Those skilled in the art of reconstructive surgery are very familiar with such fixation methods. These fixation methods include, without limitation, screw fixation, wire fixation, plate fixation, rod fixation, a hardening non-biologic cement (e.g., Palacos, available from Zimmer USA), and a biologic hardening cement-like product (e.g., Grafty's). Additionally, for smaller bone defects, the stem cell molar graft slurry may be utilized alone or in conjunction with other autologous patient bone, such as from the iliac crest.

Soft tissue defects may be similarly addressed with custom or standard collagen or connective tissue matrices or scaffolds with porosities to accept a stem cell collagen graft slurry.

Orthodontic and Maxillofacial Procedure Example

Orthodontic and the frequent accompanying maxillofacial reconstructive procedures are additional procedures where utilization of stem cell molar graft slurries formulated pursuant to the present disclosure are advantageous. Since the impacted third molar 1732 from the patient may be available for distraction, the principle concern is the formation of custom THA matrices using fresh harvested molars. However, the instant invention also makes use of stem cell molar graft slurries for use with standard, universal shaped matrices, where one of more of the patient's molars are harvested at the beginning of the reconstructive surgical procedure and processed as the other parts of the reconstructive procedure are undertaken (see e.g., FIG. 17). As discussed previously, it is not necessary to extract one or more teeth proximate to the reconstructive procedure as previously extracted teeth can be harvested and put in cryopreservation until the time each is necessary just prior to the reconstructive surgical procedure.

Exemplary grafts/matrices for use with facial reconstruction procedures may be fabricated by rapid manufacturing techniques or be prepared in bulk form to fill a particular defect. As will be discussed in more detail below, the grafts/matrices may be soaked in the stem cell molar graft slurry prior to or during the surgical reconstruction procedure while the patient is under anesthetic.

Figure 17:
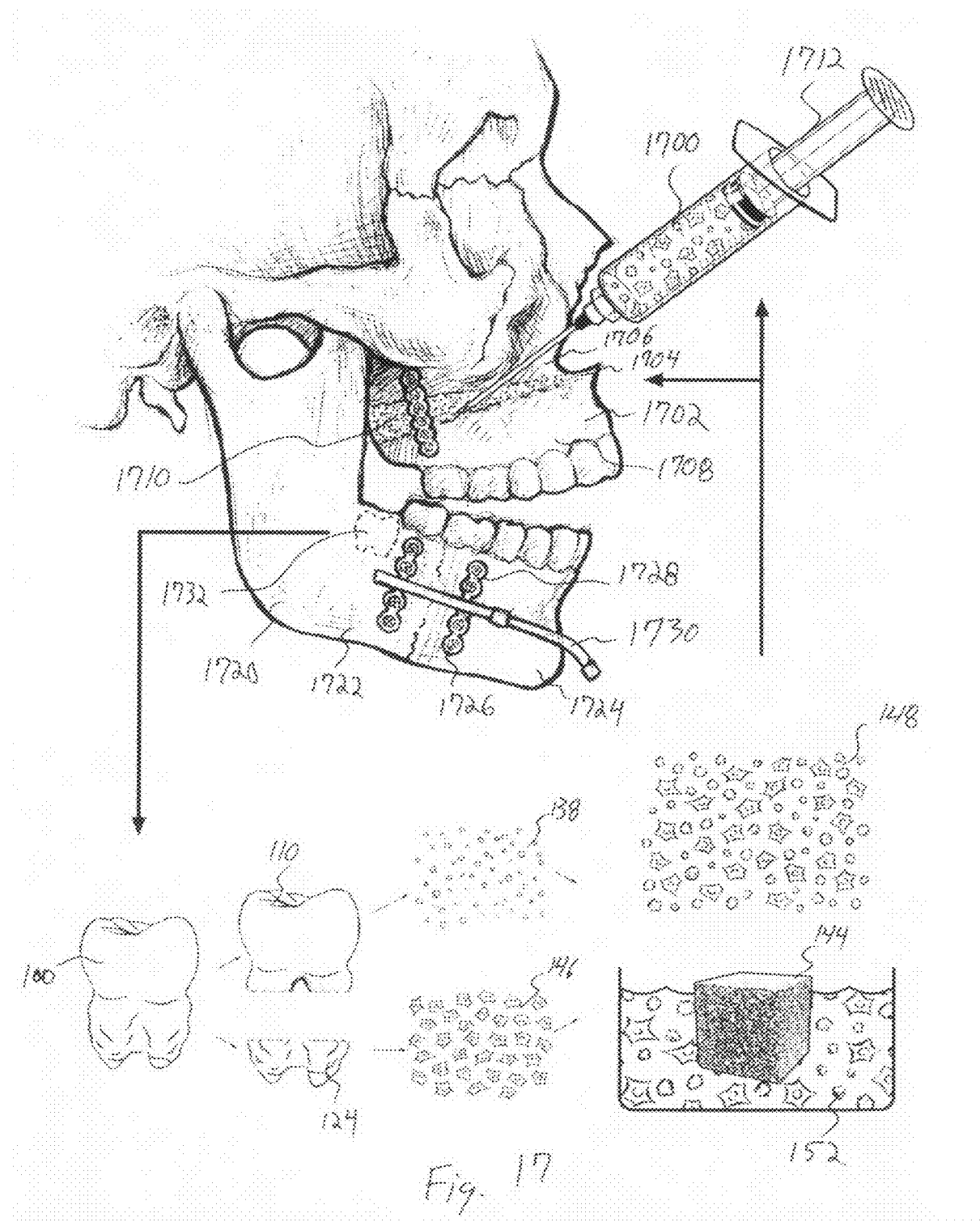
FIG. 17 is a profile view of a human skull showing physical changes resulting from a sinus lift procedure and a distraction osteogenesis procedure, both using stem cell molar bone graft slurries in accordance with the instant disclosure.

Referring to FIG. 17, an exemplary facial reconstructive procedure will be described that makes use of a molar stem cell graft slurry 1700. In this exemplary procedure, the patient is undergoing sinus lift and distraction osteogenesis procedures. It should also be noted, however, that other maxillofacial reconstructive procedures may make use of the molar stem cell graft slurry 1700 including, without limitation, ridge expansions. In sum, any gap created in maxillofacial bone is amendable for application of the molar stem cell graft slurry 1700 to facilitate bone formation proximate the bone where the slurry is located to address non-unions, fractures, ingrowth and other reconstructive bony procedures of the facial bones.

An exemplary reconstructive procedure for a sinus lift includes fracturing the maxilla 1702 along a predetermined plane 1704 in order to separate an upper portion 1706 of the maxilla from a lower portion 1708 of the maxilla that retains the patient's teeth. In this exemplary embodiment, the separation of the maxilla portions 1706, 1708 creates a wedge-shaped cavity that is filled with a bulk allograft or 3-D matrix 1710 to generally fill the cavity. In a circumstance where a 3-D matrix is utilized, the stem cell molar graft slurry 1700 is applied to the matrix so that the slurry at least partially fills the voids in the matrix in order to promote initial junction healing and eventual incorporation of the maxilla portions 1706, 1708. By way of example, the stem cell molar graft slurry 1700 is injected using a syringe 1712 into the interstices and micro-porosity of the biologic or synthetic matrix 1710. In addition, a more viscous stem cell molar graft slurry (not shown) is prepared and injected to occupy at least a portion of the junction between the maxilla portions 1706, 1708 and the 3-D matrix 1710. This latter, more viscous, bone graft slurry may be prepared with less fluid constituency, but includes the same or similar particulate sizes as used with the less viscous bone graft slurry. Alternatively, the latter, more viscous, bone graft slurry may be prepared with slightly larger particulate sizes in order to increase the ability of the bone graft flurry to remain in place. However, where a bulk allograft is utilized in lieu of the 3-D matrix, a less viscous stem cell molar graft slurry is used to at least partially fill the graft host junctions and/or into the porous matrix to promote bone reconstitution/integration.

In exemplary form, Grafty's (not shown) is utilized to seal the stem cell molar graft slurry 1700 in position at the junction between the native maxilla portions 1706, 1708 and the 3-D matrix or allograft 1710. Alternatively, Skeletal Repair System (SRS) (available from Norian, Cupertino, Calif.), is an injectable paste of inorganic calcium and phosphate that may be utilized to form a hard covering to encapsulate the bone graft slurry 1700 and retain it in the proper position. For reference purposes, SRS typically hardens in a matter of minutes and forms a carbonated apatite of low crystallinity and small grain size similar to that found in the mineral phase of bone. SRS is useful as a bone-graft substitute to augment cast treatment or internal fixation of impacted metaphyseal fractures. It should also be noted that the stem cell molar graft slurry 1700 can be added to either Grafty's or SRS to fill the pores of these materials, thereby further enhancing the potential of the patient's body to incorporate these materials as a bone substitute.

After the slurry 1700 and matrix/allograft 1710 are implanted and properly positioned, a plate 1714 is mounted to the maxilla portions 1706, 1708 and the allograft/matrix 1710 using fasteners, such as surgical screws 1716. The plate 1714 ensures that there are static interfaces between the maxilla portions 1706, 1708 and the allograft/matrix 1710, thereby enabling the stem cell molar graft slurry 1700 to promote bone formation without dynamic shifting of the interfaces.

Because the molar graft slurry 1700 is operative to facilitate bone formation in any gap created between bone, a distraction osteogenesis procedure also uses the slurry. In exemplary from, the mandible 1720 is fractured to create a rear 1722 and a forward portion 1724. In this exemplary procedure, the fracture is made vertically in between the first and second molar. However, those skilled in the art will understand that other lines of fracture may be chosen based upon the unique circumstances presented by patients' anatomies. It should be noted that prior to the mandible 1720 fracture, surgical plates 1726 are mounted to what will be the rear and forward portions 1722, 1724 using surgical screws 1728. These plates 1726, as will be discussed in more detail below, ensure proper alignment of the mandible 1720 post fracture and also operate to create a vise that retains the matrix/allograft between the mandible portions 1722, 1724.

After the fracture of the mandible 1720 is accomplished, the rear and forward portions 1722, 1724 are separated from one another, thereby creating a cavity, to allow insertion of a 3-D matrix or allograft (not shown). Similarly to the sinus lift procedure discussed immediately above, the 3-D matrix or allograft is inserted into the cavity and a stem cell molar graft slurry formulated pursuant to the instant disclosure is retained within the interstices of the matrix/allograft. In addition, autograft and bone graft extenders along with growth factors and other healing agents can be added to enhance the osteotomy or distraction procedures to optimize desired healing and bony union. After the stem cell molar graft slurry and the matrix/allograft are in position, a wire 1730 is connected to the plates 1726 mounted to both mandible portions 1722, 1724 and tensioned on order to pull the plates toward one another and sandwich the matrix/allograft therebetween in order to retain the matrix/allograft in a compression fit. Alternatively, or in addition, the surgeon may use a plate that is concurrently mounted to the matrix/allograft and one or both of the mandible portions 1722, 1724 to ensure proper alignment of the mandible and static interfaces between the matrix/allograft and the mandible portions 1722, 1724.

It should also be noted that the foregoing mandible lengthening procedure may be carried out using an Ilizarov device (not shown). In such a circumstance, the Ilizarov device is mounted to the mandible, followed by a calculated fracture of the mandible. The Ilizarov device is thereafter manipulated to lengthen the mandible as the bone forms at the fracture location. In this procedure as well, the molar graft slurry 1700 is injected proximate the fracture location at the time of the initial fracture and subsequently at periodic intervals to speed bone formation at the fracture location and decrease the time necessary to lengthen the mandible.

Cleft Palate Example

Referring to FIG. 18-20, another exemplary use of a stem cell molar graft slurry formulated in accordance with the instant disclosure is in bone replacement cleft palate surgeries. Somewhat unique to cleft palate surgeries and some facial surgeries in general is the fact that the surgical procedure takes place in the same oral cavity as the primary source for the stem cells and teeth comprising the bone graft slurry. As discussed previously, aberrant and/or unerupted teeth may need to be removed prior to or during the surgical reconstruction procedure. However, it should be noted that the exemplary cleft palate reconstruction procedure need not exclusively utilize the stem cells and/or teeth from the patient.

A cleft palate is due to the failure of fusion of the maxillary and medial nasal processes (formation of the primary palate). In most cases, a cleft lip is also present. Treatment procedures can vary with the age of the patient, where a majority of maxillofacial procedures are carried out on juveniles between the ages of 10-12 when growth is less influential as deciduous teeth are replaced by permanent teeth, thus saving the juvenile from repeated corrective surgeries. But, often a twenty-year term of care for the child born with a cleft lip and palate is necessary.

Within the first two to three months after birth, surgery is performed to close the cleft lip. Then a multitude of boney surgeries are needed depending on the defect. To repair the palate 1800, the boundaries of the palate cavity 1802 are cleaned and soft tissue removed to expose the bone. Thereafter, the cavity 1802 is filled with THA particles 1816 and a stem cell molar graft slurry 1804, formulated in accordance with the instant invention, using a syringe 1806. One or more fastening plates 1808 are mounted to the palate to retain the palate in position. Soft tissue 1814 is grafted to cover the stem cell molar graft slurry 1804 and correspondingly hold the slurry within the cavity 1802 post injection. Alternatively, other autogenous tissue or small intestinal submucosa (SIS) or surrounding advancible tissues may be used to close and contain the grafted region.

Though not always necessary, it is also within the scope of the disclosure to implant a custom 3-D THA matrix or autograft or allograft matrix fortified with stem cell molar graft slurry to at least partially occupy the cavity 1802.

In other surgical procedures, an active orthopedic appliance is secured to the cleft segments 1810, 1812 and engineered to directly transport them into proper alignment (e.g., Latham-type appliance). The Latham is surgically inserted by use of pins during the juvenile's fourth or fifth month. As is understood by those skilled in the art, a cavity exists between the palate segments. This cavity may be injected with the stem cell molar graft slurry at the time of appliance placement, with the surrounding soft tissue being operative to adequately contain the slurry injection. After, the Lantham is in place, the doctor, or parents, turn a screw daily to bring the cleft segments 1801, 1812 together to assist with future lip and/or palate repair. At any time prior to Lantham removal, the doctor may inject stem cell molar graft slurry into the cavity to facilitate bone formation and closing of the palate.

Formulating an exemplary stem cell molar graft slurry for use with cleft palate reconstruction and other facial reconstruction procedures preferably includes using an autologous, unfrozen, stem cell source. In this manner, the stem cell molar graft slurry is prepared the as soon as possible before the planned surgery and kept refrigerated until use. In an exemplary circumstance, the stem cells are harvested from the cleft palate patient just prior to the cleft palate reconstructive surgical procedure under the same general anesthesia by the coordinated efforts of a surgical team composed of maxillofacial and orthodontic surgeons. This molar or tooth harvesting procedure provides fresh, unaltered stem cells without the need for cryopreservation, which can result in stem cell number loss or pluripotency loss if stem cell duplication is necessary.

Additionally, it may be advantageous to combine the hydroxyapatite from the patient's teeth separate or along with autograft bone to fabricate 3-D replacement graft scaffolds prior to implanting the 3-D scaffold, the stem cell molar graft slurry is applied by soaking the scaffold in the slurry (if less viscous) or by applying a more viscous bone graft slurry to the exterior of the 3-D graft, where the stem cells (and possibly other patient autologous growth factors) are absorbed by the microporosity to facilitate bulk graft incorporation and vascularization due to the augmented biology. The fabricated 3-D graft, if utilized, is mounted to the native tissue (e.g., host bone) being spanned using a standard mini fragment AO fixation device (available from Synthes USA) titanium plate or with screws in circumstances where the host bone and the 3-D graft have been predrilled.

As with the foregoing examples, it may be advantageous to utilize a bone hardening graft material, such as Graftys, in order to hold the slurry in place when the voids around the graft are to be injected and the slurry is to be maximally contained.

Cleft Palate Maxilla Widening Example

At about age five, on occasion, active orthodontics are necessary to widen and even protract the maxilla. The oral and maxillofacial surgeon then should determine whether an alveolar cleft is present. If so, the alveolar cleft is typically closed, along with any residual oral nasal fistulas. In other words, for patients with a cleft palate and an alveolar cleft, the surgical procedure involves partitioning the mouth and nose by grafting.

The oral and maxillofacial surgeon is desirous to provide a framework that supports bone formation at the cleft site, thereby providing a substrate for the eruption of the proximate teeth. Flaps are elevated, which permit direct closure of the nasal mucosa, and allow placement of the bone graft comprising an allograft/matrix and stem cell molar graft slurry to complete closure of the palate with a "water tight" layer of oral-attached mucosa. While various homografts and alloplasts are currently used for purpose, the material of choice is autologous bone, which may also be used with the stem cell bone graft slurry formulated pursuant to the instant disclosure. Autologous bone may be harvested from the ileum, calvaria, mandible, tibia, or rib, for example. The foregoing surgical reconstruction of the nasal aperture provides support for the alar base and a solid foundation for future nasal reconstruction.

After grafting, the orthodontist develops proper arch form and monitors the eruption of teeth adjacent to the grafted cleft. Occasionally the cuspid requires surgical exposure and orthodontic traction, and from time to time, attached tissue grafting is indicted. Accordingly, the stem cell molar graft slurry of the instant disclosure, along with autologous bone and growth factors, may be used to address these needs.

Often, the cleft palate patient has a congenitally absent lateral incisor (i.e., a cleft dental gap). One approach is to allow the cuspid to erupt into its proper anatomic position while maintaining the lateral edentulous position. When growth is completed, an osseointegrated implant can be placed. This technique helps maintain proper arch form and tooth mass, thus providing support for the overlying facial soft tissues. Additionally, any horizontal maxillary deficiency that presents itself can be treated in early adolescent with osteodistraction. Simply but, stem cell molar graft slurries formulated in accordance with the instant disclosure teamed with Illizarov techniques are useful in carrying out an osteo-distraction. It should also be understood by those skilled in the art that, at the time of surgery, residual fistulas and additional bone grafting may be performed.

Tooth Crown Example

An exemplary bone augmentation application for stem cell molar graft slurries formulated in accordance with the instant disclosure includes preparation of the jawbone for dental crowns. As is known to those skilled in the art, placement of dental crowns requires enough jawbone to support them. In a typical situation of a chronically lost single tooth missing for several years, there may not be enough bone to support the desired crown. Often, the patient does not have enough bone because of tooth loss from periodontal disease, injury or trauma, or a developmental defect. If the jawbone is too short (up and down), too narrow (side to side), or both, a bone augmentation procedure is necessary to add bone mass to the jawbone before dental implants can be placed. Current bone graft procedures involve extracting bone from other parts of the patient's body (chin, ramus, hip, or tibia) or implanting bone-like materials into the jawbone, and waiting for the grafted material to fuse with existing jawbone over several months.

Preexisting procedures may continue to be used with stem cell molar graft slurry fabricated in accordance with the instant disclosure. Initially, a viscous stem cell bone graft slurry is injected proximate the interface between the jawbone and the implanted materials to facilitate bulk graft incorporation and vascularization. Over the course of healing, less viscous stem cell molar graft slurries may be injected proximate the graft to accelerate fusion.

Alternatively, stem cell molar graft slurries fabricated in accordance with the instant disclosure provide an alternative to harvesting the patient's bone. For example, if the patient has an unerupted third molar, a family member that could donate such a molar, or access to an HLA-typed molar, this molar provides a ready source for stem cells and hydroxyapatite utilized to fabricate a 3-D scaffold for anchoring at the recipient site. Hydroxyapatite from the harvested/donated molar, along with autograft bone, may be utilized to fabricate a 3-D replacement graft scaffold. Prior to implanting the 3-D scaffold, the stem cell molar graft slurry formulated pursuant to the instant disclosure is applied by soaking the scaffold in the slurry (if less viscous) or by applying a more viscous bone graft slurry to the exterior of the 3-D graft, where the stem cells are absorbed by the microporosity.

To position the 3-D scaffold at the recipient site, the dentist first drills holes in the existing bone to cause bleeding. The 3-D scaffold is thereafter anchored to the jawbone using titanium screws in a similar way to present day harvested bulk bone graft procedure. Likewise, a stem cell molar graft slurry is fabricated, preferably using portions of the patient's molar and stem cells. This stem cell molar graft slurry is then injected into the scaffold, followed by covering the scaffold with slurry and a protective membrane (or other protective covering) over both the scaffold and slurry in order to prevent the stem cells from migrating away from the scaffold. As should be understood by those skilled in the art, the underlying bleeding of the jawbone helps the vascularization of this bone graft and delivers growth factors for healing. In addition, the stem cell bone graft slurry may be cryogenically preserved and later injected periodically at the grafting site in order to accelerate fusion.

Ligament/Cartilage Example

Referring to FIG. 1, in addition to the foregoing examples where stem cell molar graft slurries were fabricated for treatment of various bone growth issues, it should be understood that the instant disclosure also combines stem cells 136 harvested from teeth 100 with soft tissue 134 also derived from harvested teeth to produce a stem cell collagen molar graft slurry 146. When combined, the stem cells 136 and soft tissue 134 from the harvested tooth 100 create a stem cell soft tissue graft slurry for use in treating ligamentous and cartilaginous loss.

The process for extracting soft tissue from teeth, as well as periodontal ligament, is well known in the art (See *Isolation, cultivation and characterization of stem cells in human periodontal ligament*, Molnár B, Kádár K, Király M, et al Fogorv Sz., 2008 August; 101(4):155-61, the disclosure of which is incorporated herein by reference). Accordingly, only for purposes of brevity, a detailed discussion of isolating soft tissue from teeth and the periodontal ligament has been omitted.

A stem cell soft tissue graft slurry (stem cell collagen molar slurry) formulated in accordance with the instant disclosure is, when injected in vivo, operative to form connective tissue for ligament and other soft tissue injuries and pathologies. The consistency of the tissue/stem cell mixture will also vary with application and containment needs. A 3:1 collagen to stem cell ratio may be desirable for severely frayed tendon injuries or where the tendon ends are becoming separated. For a segmental replacement of a tendon defect by a molar derived collagen matrix, however, the ratio may be 3:1 stem cells to collagen.

Referring to FIG. 21, an exemplary circumstance involves a surgical procedure to repair a partially torn Achilles tendon 2100. In such a circumstance, conservative treatment may be desired in order to return the patient to normal functionality as soon as possible. However, the biology of healing must be enhanced to improve tendon healing and thereby decrease the disabling time course of the injury. To enhance the biology of healing, a stem cell soft tissue graft slurry may be injected proximate the Achilles tendon to promote tendon regrowth.

Referring to FIG. 22, in an alternate, more severe, circumstance where tendon restructuring is necessary, a stem cell soft tissue graft slurry 2102 may be injected subcutaneously via a syringe 2104 into the tendon to be restructured or in the peritendon region. The soft tissues surrounding the tendon or peritendon region are operative to retain the stem cell soft tissue graft slurry 2102 in location. The tendon is appropriately braced to protect the healing tendon zone, but for a shortened period of time due to the enhanced biology stimulated by the stem cell collagen graft slurry 2102.

In formulating a stem cell soft tissue graft slurry in accordance with the instant disclosure, the slurry may be supplemented with the patient's autologous blood products or concentrates to provide certain growth factors (e.g., tumor necrosis factor (TNF) and interleukin (IL)) to further stimulate the desired soft tissue healing.

In the alternative, the stem cell soft tissue graft slurry 2102 may be applied to a cell free, tooth derived, collagen scaffold 2106 mounted to the ends of the tendon dehiscence to repair the gap between the end of the torn Achilles tendon. Exemplary collagen scaffolds 2106 for use in tendon repair may be tubular and sutured to the tendon at opposite ends. The scaffold 2106 is preferably injected with a low viscosity solution of stem cell collagen molar graft slurry 2102 operative to penetrate the porosity of the scaffold. Alternatively, the scaffold 2106 may be soaked in the slurry 2102 prior to implantation, again to allow the slurry to adequately penetrate the interstices of the scaffold.

Arthritis Treatment Example

In a circumstance where cartilage restructuring is desired, a stem cell molar collagen slurry formulated pursuant to the instant disclosure may be injected directly into joints. In such a circumstance, the soft tissue of the joint capsule is operative to retain the stem cell soft tissue graft slurry in location. Alternatively, or at the same time, a soft tissue stem cell slurry may be injected into the joint capsule to treat arthritic and cartilaginous pathologies. The injection may be carried out by simple sterile injection via syringe and the time of injection is not necessarily critical. For instance, the injection into the joint capsule may occur at the end of arthroscopic procedure, much like a current steroid injection. In addition, the injection may occur in conjunction with a steroid injection, and/or injection of platelet concentrates, and/or appropriate growth factors to promote the desired healing.

Veterinary Applications

While the foregoing examples all related to a combination of human stem cells and either hard or soft tissues taken from human teeth, the methods and corresponding formulations are equally applicable to species other than humans. For example, the instant disclosure provides a solution for fracture fixation, fusion, reconstructive, prosthetic ingrowth, and other orthopedic applications in veterinary applications as well. The veterinary orthopedic and soft tissue applications mirror those of the human discussed above and otherwise. Likewise, the harvesting of one or more teeth from animals depends upon species and the corresponding dental anatomy.

Soft tissue applications include ligamentous and other soft tissue applications (reconstruction and healing) where the stem cells are used in conjunction with soft connective tissue (from the molar or from allogenic sources). As with human applications, injection of a stem cell soft tissue slurry into an animal (non-human) joint cavity with or without additional autologous blood cells and plasma is operative to provide enhanced healing.

In non-human mammalian molar teeth, the pulp is similarly located at the center, or core of the tooth and in the unerupted state this pulp contains stem cells like in a human molar. After eruption of the molar, the pulp region includes connective tissue, nerves, and blood vessels that nourish the tooth. But, stem cells remain for a period of time in exfoliated molar teeth as they do in human exfoliated deciduous teeth. As in the human tooth, special cells in the pulp, called "odontoblasts" form dentin.

The majority of a mammalian tooth is made up of dentin, which surrounds the pulp. Primary dentin is dentin that is formed before tooth eruption; secondary dentin is dentin that is continually formed throughout the life of the tooth. As the secondary dentin forms, the pulp chamber reduces in size. The dentin of the crown is encased in enamel and the dentin of the root is covered by cementum. Dentin consists of 50-85% inorganic hydroxyapatite crystals, combined with organic matrix (mostly collagen) and water. Intertubular dentin (primary structural component) is comprised of hydroxyapatite embedded in a collagen matrix. Peritubular dentin is a collagen free hypermineralized tubular wall. Dental tubules filled with odontoblasts form the interface between the dentin and the pulp.

The dense, hard external covering of mammal teeth is enamel, which consists of more than 95% of the mineral hydroxyapatite. A hallmark of mammals is that the enamel characteristically, consists of a complex of bumps (cusps) and ridges, which together increase the surface area of the tooth. Therefore, the ground tooth for use as a graft comprises, as a majority, hydroxyapatite with some collagen content. The alveolar bone forms the jaw and the sockets into which the roots of the teeth extend. The periodontal ligaments are a collection of connective tissue that helps to hold the tooth in the socket. These ligaments attach to the cementum of the tooth and the alveolar bone. Simply put, the same human harvesting preservation and uses are possible in most mammals. Because of some unique dental anatomy for certain species, variability for ideal harvest timing (unerupted, premolar, shed teeth, etc), preservation and uses in animals of similar species and compatibility (ABO and or HLA) may be required.

Equine Examples

A foal typically will have a total of 16 teeth (four incisors or front teeth, and 12 premolars or back teeth). At four to six weeks of age, four more incisors will erupt and at approximately six to nine months of age the last set of up to 24 deciduous incisors will erupt. All of these teeth are replaced during the time up to 5 years of age. Consequently, there is a constant eruption and loss of deciduous teeth, overlapping with eruption of the permanent teeth during this period. Eventually up to 44 permanent teeth might be present in the horse's mouth—half of these are in the mandible and the other half are in the maxilla. Unlike dogs, cats, and humans, equine teeth continue to erupt throughout life.

At the same time, rudimentary premolar wolf teeth (referred to as "pm1") may erupt in front of the upper cheek teeth. These premolar wolf teeth are small premolars which appear on the mandible above and usually slightly ahead of the molars. But in some horses, especially the standard bred horse, it is not uncommon to also get wolf teeth in the maxilla (and often "blind" unerupted). These teeth are vestigial, that is, they serve no purpose and may interfere with biting of the horse. It is therefore advisable to remove wolf teeth while the horse is still young as these teeth will eventually fuse with the bones of the skull making extraction far more difficult as the horse gets older. These wolf teeth, particularly the unerupted "blind" are an ideal source of molar pulp (and soft tissue containing stem cells) and hard tooth matter for use in formulating exemplary stem cell molar grafts for bone and soft tissue.

At twelve months of age, the first of the permanent cheek teeth begin to erupt, so it is a good time to ensure that normal eruption is occurring and to identify any other problems. From 1 year to 6 years of age horses will shed their first set of 24 deciduous teeth and up to 44 permanent teeth will erupt through the gums. The structure of the chewing teeth (premolars and molars) in advanced horses is that the crowns are elongated relative to primitive mammals, so that they become high-crowned (i.e., hypsodont). Highcrowned horse teeth have several layers of folded enamel, forming "lakes" or fossettes on the chewing surface. The extended period of crown growth is accomplished by regulation of the stem cells containing cervical loop. There are also continuously growing teeth in which the cervical loop is maintained throughout the lifetime of the animal. The longer the stem cell niche is maintained and differentiated progeny of the stems cells are produced, the higher the crown.

A multitude of opportunities exist to harvest tooth and stem cell materials from equine animals. For example, unerupted wolf teeth are an excellent source of both tooth hydroxyapatite and stem cells. And the stem cell niche in the cervical loop of the highcrowned molars represent a source of stem cells available at any time during the horse's life.

Since 2003, veterinarians have used autologous Human adipose derived mesenchymal stem cells (ADMSCs) to treat tendon and ligament injuries and joint disease in horses on a commercial basis (e.g., Vet Stem, BioScience, Ltd. UK). As these cells are classified as "minimally manipulated," these autologous stem cell therapies do not require FDA approval.

Studies and multiple anecdotal clinical experience demonstrate that autologous ADMSC therapy is of clinical benefit in horses with orthopedic conditions. ADMSC has also shown therapeutic success in equine tendonitis demonstrating statistically significant improvement in inflammatory cell infiltrate, collagen fiber uniformity, polarized collagen fiber crimping, overall tendon healing score, and collagen oligomeric matrix protein scores.

Equine Examples

Figure 23:
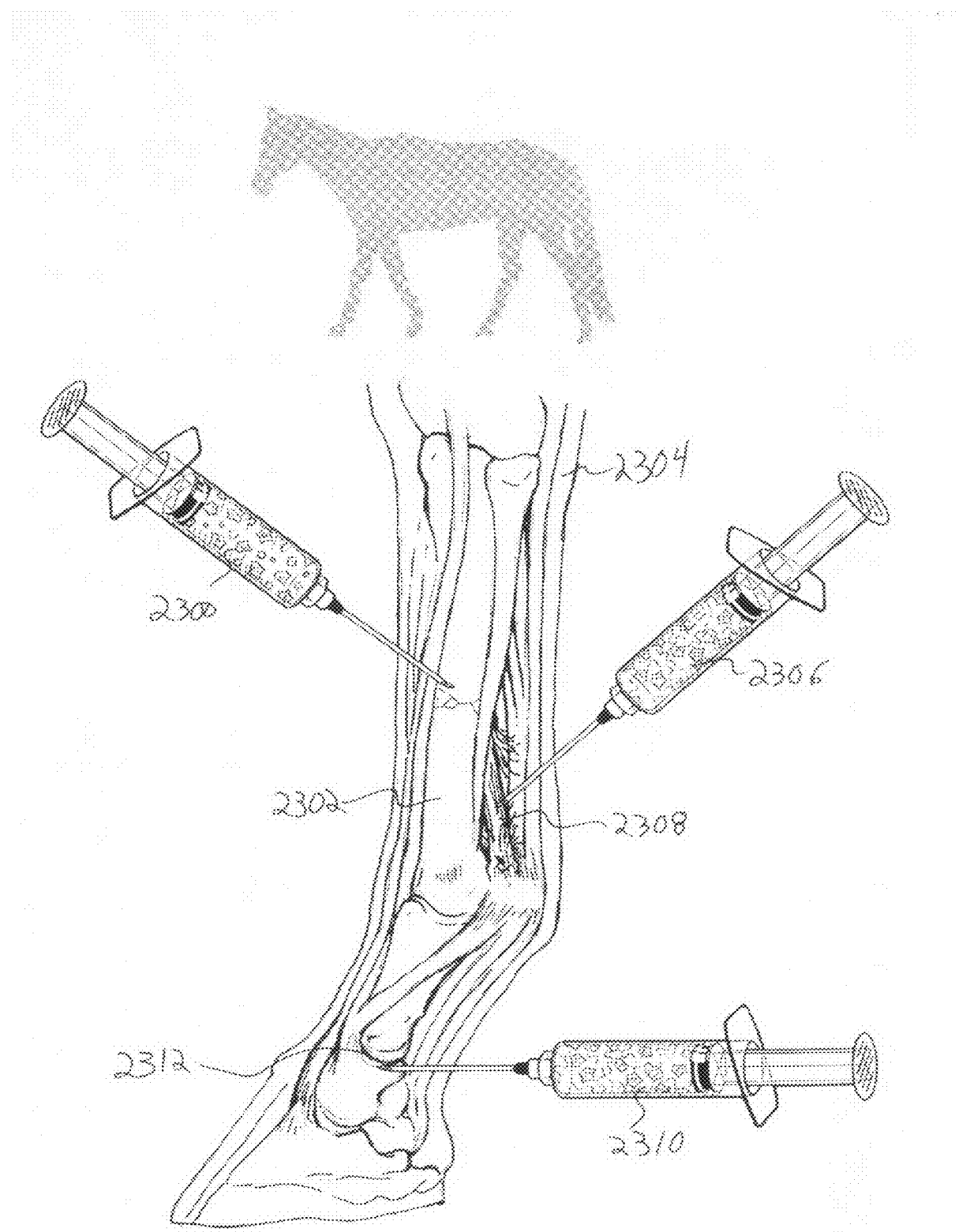
FIG. 23 is a profile view of an equine lower leg showing bones, muscles, and connective tissues, where stem cell slurries were specifically formulated for certain purposes (e.g., bone, soft tissue, connective tissue, etc.) and injected to treat certain ailments.

Referring again to FIG. 23, successful equine fracture repair is dependent on the ability of the horse to generate enough new bone in time to stabilize the fracture before the onset of complications. An exemplary use of a stem cell molar bone graft slurry 2300 with appropriate auotologous additive is shown in FIG. 23 being injected into a non-displaced fracture of a lower leg bone 2302 of a horse 2304. As discussed above, the stem cell molar bone graft slurry 2300 is formulated to include stems cells from one or more equine teeth in addition to hard particulate matter derived from equine teeth. Preferably, both the stem cells and tooth particulate matter are taken from the equine to be treated with the stem cell molar bone graft slurry 2300. However, close matches between equines may provide for withdrawal of stem cells from teeth of closely related animals and thereafter implantation/injection of the stem cell molar bone graft slurry 2300 without complications stemming from immune response and rejection of the stem cells and tooth particulate. Similarly, and not inclusively, reconstructive application, non-union treatments, fusions could all be applications to one of normal skill in the area of equine orthodontic, and orthopedic bone procedures.

A further use of stem cells derived from an equine donor includes a stem cell molar soft tissue graft slurry 2306 formulated for injection proximate a lower leg injured ligament 2308 of a horse 2304. Similarly to ligamentous application discussed previously as to humans, the stem cells and soft tissue are extracted from a donor tooth and later combined to create the soft tissue slurry 2306. Depending upon the frequency of the injection and the site of injection, the slurry 2306 may be modified to include growth factors and other native additives, in addition to viscosity modifiers, in order to ensure the slurry is properly retained in the region of interest. Stem cell molar soft tissue slurries 2306 derived from equine teeth and formulated in accordance with the instant invention may be useful for the treatment of ligamentous injuries that plague horses, particularly those that are common to competitive jumping and racing horses.

In addition, an even further use of stem cells derived from an equine donor includes a stem cell molar slurry 2310 formulated for injection proximate an arthritic joint 2312 of the lower leg of a horse 2304. Similarly to joint injection applications discussed previously as to humans, the stem cells and pertinent soft tissue extracts from an equine donor tooth are utilized to create a stem cell slurry 2310. Depending upon the frequency of the injection and the site of injection, the slurry 2310 may be modified to include growth factors and other native additives, in addition to viscosity modifiers.

Canine Examples

Puppies have 28 teeth, while adult dogs have 42. The first deciduous teeth to come in are the canine teeth, followed by the incisors, premolars, and molars. Puppies generally start to lose the deciduous teeth at 2-3 months of age. Puppy teeth contain stem cells and hydroxyapatite from the puppy teeth may be harvested and stored as the permanent deciduous teeth and canines erupt. But before the incisors, premolars, and molars erupt, in precursor form within the alveolar bone, the teeth may be harvested in a similar fashion to that described above for human teeth. In addition, when permanent and deciduous teeth are present at the same site, the deciduous tooth may be surgically removed to provide another source for tooth, soft tissue, and stem cell harvest. Consequently, hard tooth constituents, stem cells, and connective tissues are preferably harvested at the time of the orthopedic and soft tissue repair procedures. However, because of the opportunity that exists when canines are young, the disclosure provides a means of harvesting puppy teeth and cryogenically preserving these teeth so that later utilization of the stem cells, hard constituents, and soft tissue constituents may be used in later life of the canine for one or more orthopedic and soft tissue repair procedures.

Figure 24:
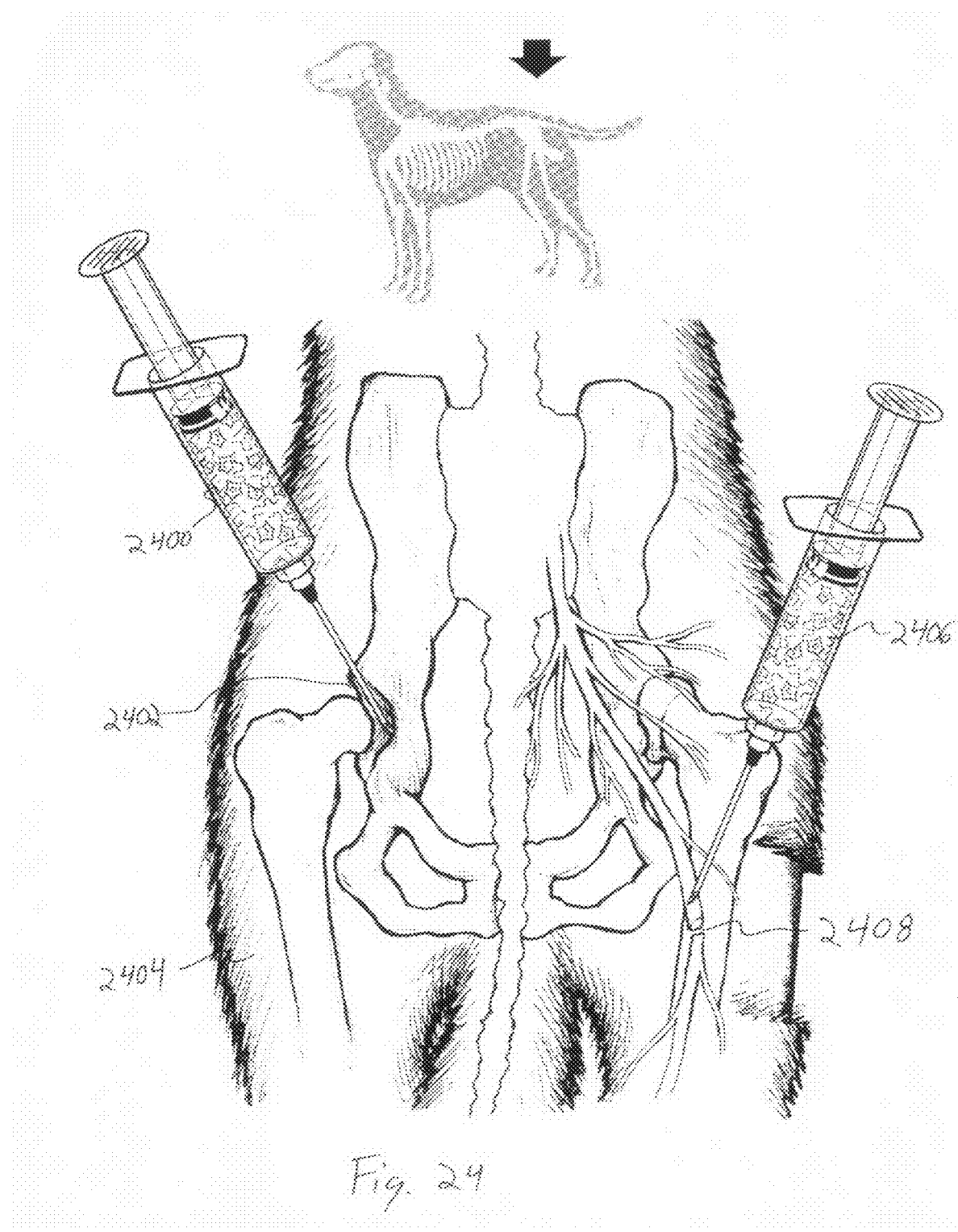
FIG. 24 is frontal view of a canine pelvis, where stem cell slurries were specifically formulated for certain purposes (e.g., bone, soft tissue, connective tissue, nerves, etc.) and injected to treat certain ailments.

Referring to FIG. 24, an exemplary use of a stem cell slurry 2400 formulated in accordance with the instant disclosure for injection proximate an arthritic hip joint 2402 of a canine 2404. Similarly to joint injection applications discussed previously as to humans, the stem cells extracted from a canine donor tooth are utilized to create a stem cell bone slurry or stem cell soft tissue slurry containing a large population of stem cells available for conversion into soft tissue, such as the cartilage providing a bearing surface between the femur and acetabulum. Depending upon the frequency of the injection and the site of injection, the slurry 2400 may be modified to include growth factors and other native additives, in addition to viscosity modifiers. Likewise, the stem cell slurry 2400 may also be used to treat canine cartilage and soft tissue joint pathologies.

Another exemplary use of a canine stem cell slurry includes a stem cell collagen slurry 2406 used to repair nerve injury where both stem cell precursors and collagen and connective tissue material is needed for nerve regeneration. In exemplary from, the stem cell collagen slurry 2406 is formulated from canine stem cells and the soft tissue extracted from one or more canine teeth. Preferably, the stem cells and soft tissue are taken or have been taken from the canine patient. The stem cell collagen slurry 2406 is injected proximate the nerve damage 2408 (in this case, a nerve tear) in order to promote nerve regeneration.

Alternatively, a canine stem cell collagen slurry may also be injected proximate ligamentous and tendon injuries in order to promote ligament and tendon repair. Those skilled in the art will readily understand the various applications for a stem cell collagen slurry based upon the plethora of injuries and degradations suffered by canines.

In accordance with the present disclosure, an exemplary use of a stem cell molar bone graft slurry (not shown) with appropriate auotologous additive is to treat a non-displaced fracture of bone of a canine. Such an exemplary stem cell molar bone graft slurry is formulated to include canine stems cells from one or more canine teeth, in addition to hard particulate matter derived from one or more canine teeth. Preferably, both the stem cells and tooth particulate matter are taken from the canine to be treated with the stem cell molar bone graft slurry. However, close matches between canines may provide for withdrawal of stem cells from teeth of closely related animals and thereafter implantation/injection of the stem cell molar bone graft slurry without complications stemming from immune response and rejection of the stem cells and tooth particulate. Similarly, and not inclusively, reconstructive application, non-union treatments, fusions could all be applications to one of normal skill in the area of canine orthodontic, and orthopedic bone procedures.

While the foregoing examples have been described with respect to canines, it is also within the scope of the disclosure to harvest feline teeth and utilized one or more of the soft tissue, stem cells, and hard constituents of a feline tooth to formulate a stem cell slurry. Those skilled in the art will be readily able to formulate a stem cell slurry for a feline based upon the foregoing disclosure. Consequently, for purposes of brevity, a more detailed explanation has been omitted.

Persons of skill in the art will understand that the foregoing methods are also applicable to non-human mammals and reptiles, including utilization of allograft bone sources and synthetic sources of scaffold. Moreover, the disclosure may be used to replace soft tissue, such as collagen, ligament tendon and cartilage, in addition to or instead of bone.

Following from the above description and disclosure summaries, it should be apparent to those of ordinary skill in the art that, while the methods and apparatuses herein described constitute exemplary embodiments of the present disclosure, the disclosure contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present disclosure may exist even though they may not have been explicitly discussed herein.

What is claimed is:

1. A medical treatment composition comprising:
   physically disrupted, non-collagenase-digested tooth pulp including a plurality of stem cells; and
   a plurality of ground mammalian tooth particles.

2. The medical treatment composition of claim 1, wherein the plurality of ground mammalian tooth particles includes dentin, enamel, or mixtures thereof.

3. The medical treatment composition of claim 1, wherein the plurality of ground mammalian tooth particles includes particles of tooth derived hydroxyapatite.

4. The medical treatment composition of claim 1, wherein the plurality of ground mammalian tooth particles includes one or more endogenous or exogenous growth factors.

5. The medical treatment composition of claim 4, wherein the one or more endogenous or exogenous growth factors are chosen from transforming growth factor beta, insulin like growth factor I, insulin like growth factor II, platelet-derived growth factor, fibroblast growth factor, and bone morphogenetic proteins.

6. The medical treatment composition of claim 1, wherein the physically disrupted, non-collagenase-digested tooth pulp is selected from the group consisting of a diced tooth pulp, a minced tooth pulp, and combinations thereof.

7. The medical treatment composition of claim 1, wherein the physically disrupted, non-collagenase-digested tooth pulp is a sterilized, physically disrupted, non-collagenase digested tooth pulp, and wherein the sterilized, physically disrupted, non-collagenase digested tooth pulp includes a plurality of stem cells that are living.

8. The medical treatment composition of claim 1, wherein the plurality of stem cells includes pluripotent stem cells.

9. The medical treatment composition of claim 1, wherein the plurality of ground mammalian tooth particles have a mean particle size in the range of 5 μm to 100 μm.

10. The medical treatment composition of claim 1, wherein the plurality of ground mammalian tooth particles have a mean particle size in the range of 100 μm to 500 μm.

11. The medical treatment composition of claim 1, wherein the plurality of ground mammalian tooth particles have a mean particle size in the range of 500 μm to 1,000 μm.

* * * * *

UNITED STATES PATENT AND TRADEMARK OFFICE
CERTIFICATE OF CORRECTION

| | | |
|---|---|---|
| PATENT NO. | : 8,470,308 B2 | |
| APPLICATION NO. | : 12/655633 | |
| DATED | : June 25, 2013 | |
| INVENTOR(S) | : Ray C. Wasielewski | |

It is certified that error appears in the above-identified patent and that said Letters Patent is hereby corrected as shown below:

In the drawing sheets, consisting of Figs. 6, 7 and 8, should be deleted to be replaced with the drawing sheets, consisting of Figs. 6, 7, and 8, as shown on the attached pages.

In the Specification:

Column 1,
Lines 21-22 read "Scientific Progress and Future Research Directions (June 2001), indicate that" and should read -- Scientific Progress and Future Research Directions (June 2001) indicate that --.

Column 2,
Lines 54, 56, 58, 59 reads "Inc," and should read -- Inc., --.

Column 3,
Line 14 reads "harvested hu man tooth," and should read -- harvested human tooth, --.

Column 4,
Lines 22-23 reads "showing the sequence of utilized to" and should read -- showing the sequence of steps utilized to --.

Column 4,
Lines 61-62 read "using acementless femoral and patella components," and should read -- using cementless femoral and patella components, --.

Column 5,
Line 17 reads "FIG. 24 is frontal view of a" and should read -- FIG. 24 is a frontal view of a --.

Column 5,
Lines 47-49 read "method of...as disclosed in...the disclosure of which is incorporated herein" and should read --method of...is disclosed in...the disclosure of which is incorporated herein --.

Signed and Sealed this
Twenty-fourth Day of December, 2013

Margaret A. Focarino
*Commissioner for Patents of the United States Patent and Trademark Office*

CERTIFICATE OF CORRECTION (continued)
U.S. Pat. No. 8,470,308 B2

In the Specification:

Column 9,
Lines 47-48 read "The cells can then be spit on Matrigel" and should read -- The cells can then be split on Matrigel --.

Column 10,
Lines 1-2 read "have been used a bone graft material" and should read -- have been used as bone graft material --.

Column 10,
Line 2 reads "Oktar, et al "Histopatological-"" and should read -- Oktar, et al "Histopathological- --.

Column 11,
Lines 6-7 read "Harvesting...require additional" and should read -- Harvesting...requires additional --.

Column 11,
Lines 44-45 read "the larger the applications (such as,...) requires more cells, while" and should read -- the larger applications (such as,...) require more cells, while --.

Column 12,
Lines 60-61 read "the viscosity of the bone graft slurry 148 and soft tissue graft slurry 146 are also" and should read -- the viscosities of the bone graft slurry 148 and soft tissue graft slurry 146 are also --.

Column 13,
Lines 34-36 read "also provide initial control of bleeding...and reduce of post-operative bruising" and should read -- also provide initial control of bleeding...and reduction of post-operative bruising --.

Column 13,
Lines 36-37 read "In addition to providing...and platelet gels release mediators to help" and should read -- In addition to providing...platelet gels release mediators to help --.

Column 13,
Line 52 reads "or may be take from" and should read -- or may be taken from --.

Column 16,
Line 11 reads "THA particles other bone graft extenders 422" and should read -- THA particles, other bone graft extenders 422 and --.

Column 17,
Line 3 reads "particle sized outside of this range" and should read -- particles sized outside of this range --.

CERTIFICATE OF CORRECTION (continued)
U.S. Pat. No. 8,470,308 B2

In the Specification:

Column 18,
Line 6 reads "When open reduction and internal fixation is required for" and should read -- When open reduction and internal fixation are required for --.

Column 19,
Lines 10-11 read "slurry 902 maintains is position also" and should read -- slurry 902 maintains its position also --.

Column 19,
Lines 55-56 read "matrix/scaffold is formed...is utilized as" and should read -- matrix/scaffold formed...is utilized as --.

Column 19,
Lines 62 and 64 read "Inc," and should read -- Inc., --.

Column 21,
Lines 66-67 read "In circumstances of failing distraction or when more rapid to distraction is desired" and should read -- In circumstances of failing distraction or when more rapid distraction is desired --.

Column 22,
Line 10 reads "Arthropasy Example" and should read -- Arthroplasty Example --.

Column 22,
Lines 22-23 read "using a cement to concurrently bonding to the tibial insert 1402 to the tibia" and should read -- using a cement to concurrently bond the tibial insert 1402 to the tibia --.

Column 22,
Line 67 reads "part of the arthropasy procedure" and should read -- part of the arthroplasty procedure --.

Column 23,
Lines 40-42 read "period of time when limited weight bearing and joint motion is permitted is not so long" and should read -- period of time when limited weight bearing and joint motion are permitted is not so long --.

Column 23,
Lines 65-66 read "procedure where stem cell molar graft slurries includes" and should read -- procedure with stem cell molar graft slurries includes --.

CERTIFICATE OF CORRECTION (continued)
U.S. Pat. No. 8,470,308 B2

In the Specification:

Column 24,
Lines 8-10 read "Both of the foregoing process involve" and should read -- Both of the foregoing processes involve --.

Column 24,
Lines 12-15 read "However, after arising technology may allow for layering methods may allow scaffolds to be...built up from...layers, stacked upon one another to form the final 3-D structure that provide an" and should read -- However, arising technology may allow for layering methods, may allow scaffolds to be...built up from...layers, stacked upon one another to form the final 3-D structure that provides an --.

Column 24,
Lines 25-26 read "such as platelet jells to increase" and should read -- such as platelet gels to increase --.

Column 24,
Lines 28-29 read "create two distinct slurries one with" and should read -- create two distinct slurries, one with --.

Column 24,
Line 64 reads "the principle concern is the" and should read -- the principal concern is the --.

Column 25,
Line 52 reads "bone graft flurry" and should read -- bone graft slurry --.

Column 26,
Line 49 reads "and tensioned on order to pull the" and should read -- and tensioned in order to pull the --.

Column 27,
Line 62 reads "slurry is prepared the as soon as possible" and should read -- slurry is prepared as soon as possible --.

Column 28,
Lines 8-9 read "to fabricate 3-D replacement graft scaffolds prior to implanting the 3-D scaffold, the stem cell molar graft" and should read -- to fabricate 3-D replacement graft scaffolds. Prior to implanting the 3-D scaffold, the stem cell molar graft --.

Column 28,
Line 66 reads "be treated in early adolescent with" and should read -- be treated in early adolescence with --.

CERTIFICATE OF CORRECTION (continued)
U.S. Pat. No. 8,470,308 B2

In the Specification:

Column 28,
Line 67 reads "Simply but, stem cell molar" and should read -- Simply put, stem cell molar --.

Column 34,
Lines 8-9 read "to include canine stems cells from" and should read -- to include canine stem cells from --.

Column 35,
Lines 8-9 read "such as collagen, ligament tendon and" and should read -- such as collagen, ligament, tendon and --.

UNITED STATES PATENT AND TRADEMARK OFFICE
CERTIFICATE OF CORRECTION

| | | |
|---|---|---|
| PATENT NO. | : 8,470,308 B2 | Page 1 of 6 |
| APPLICATION NO. | : 12/655633 | |
| DATED | : June 25, 2013 | |
| INVENTOR(S) | : Ray C. Wasielewski | |

It is certified that error appears in the above-identified patent and that said Letters Patent is hereby corrected as shown below:

In the drawing sheets, consisting of Figs. 6, 7 and 8, should be deleted to be replaced with the drawing sheets, consisting of Figs. 6, 7, and 8, as shown on the attached pages.

In the Specification:

Column 1,
Lines 21-22 read "Scientific Progress and Future Research Directions (June 2001), indicate that" and should read -- Scientific Progress and Future Research Directions (June 2001) indicate that --.

Column 2,
Lines 54, 56, 58, 59 read "Inc," and should read -- Inc., --.

Column 3,
Line 14 reads "harvested hu man tooth," and should read -- harvested human tooth, --.

Column 4,
Lines 22-23 read "showing the sequence of utilized to" and should read -- showing the sequence of steps utilized to --.

Column 4,
Lines 61-62 read "using acementless femoral and patella components," and should read -- using cementless femoral and patella components, --.

Column 5,
Line 17 reads "FIG. 24 is frontal view of a" and should read -- FIG. 24 is a frontal view of a --.

This certificate supersedes the Certificate of Correction issued December 24, 2013.

Signed and Sealed this
First Day of April, 2014

Michelle K. Lee
*Deputy Director of the United States Patent and Trademark Office*

CERTIFICATE OF CORRECTION (continued)
U.S. Pat. No. 8,470,308 B2

In the Specification:

Column 5,
Lines 47-49 read "method of...as disclosed in...the disclosure of which is incorporated herein" and should read -- method of...is disclosed in...the disclosure of which is incorporated herein --.

Column 9,
Lines 47-48 read "The cells can then be spit on Matrigel" and should read -- The cells can then be split on Matrigel --.

Column 10,
Lines 1-2 read "have been used a bone graft material" and should read -- have been used as bone graft material --.

Column 10,
Line 2 reads "Oktar, et al "Histopatological-"" and should read -- Oktar, et al "Histopathological- --.

Column 11,
Lines 6-7 read "Harvesting...require additional" and should read -- Harvesting...requires additional --.

Column 11,
Lines 44-45 read "the larger the applications (such as,...) requires more cells, while" and should read -- the larger applications (such as,...) require more cells, while --.

Column 12,
Lines 60-61 read "the viscosity of the bone graft slurry 148 and soft tissue graft slurry 146 are also" and should read -- the viscosities of the bone graft slurry 148 and soft tissue graft slurry 146 are also --.

Column 13,
Lines 34-36 read "also provide initial control of bleeding...and reduce of post-operative bruising" and should read -- also provide initial control of bleeding...and reduction of post-operative bruising --.

Column 13,
Lines 36-37 read "In addition to providing...and platelet gels release mediators to help" and should read -- In addition to providing...platelet gels release mediators to help --.

Column 13,
Line 52 reads "or may be take from" and should read -- or may be taken from --.

Column 16,
Line 11 reads "THA particles other bone graft extenders 422" and should read -- THA particles, other bone graft extenders 422 and --.

CERTIFICATE OF CORRECTION (continued)
U.S. Pat. No. 8,470,308 B2

In the Specification:

Column 17,
Line 3 reads "particle sized outside of this range" and should read -- particles sized outside of this range --.

Column 18,
Line 6 reads "When open reduction and internal fixation is required for" and should read -- When open reduction and internal fixation are required for --.

Column 19,
Lines 10-11 read "slurry 902 maintains is position also" and should read -- slurry 902 maintains its position also --.

Column 19,
Lines 55-56 read "matrix/scaffold is formed...is utilized as" and should read -- matrix/scaffold formed...is utilized as --.

Column 19,
Lines 62 and 64 read "Inc," and should read -- Inc., --.

Column 21,
Lines 66-67 read "In circumstances of failing distraction or when more rapid to distraction is desired" and should read -- In circumstances of failing distraction or when more rapid distraction is desired --.

Column 22,
Line 10 reads "Arthropasy Example" and should read -- Arthroplasty Example --.

Column 22,
Lines 22-23 read "using a cement to concurrently bonding to the tibial insert 1402 to the tibia" and should read -- using a cement to concurrently bond the tibial insert 1402 to the tibia --.

Column 22,
Line 67 reads "part of the arthropasy procedure" and should read -- part of the arthroplasty procedure --.

Column 23,
Lines 40-42 read "period of time when limited weight bearing and joint motion is permitted is not so long" and should read -- period of time when limited weight bearing and joint motion are permitted is not so long --.

Column 23,
Lines 65-66 read "procedure where stem cell molar graft slurries includes" and should read -- procedure with stem cell molar graft slurries includes --.

CERTIFICATE OF CORRECTION (continued)
U.S. Pat. No. 8,470,308 B2

In the Specification:

Column 24,
Lines 8-10 read "Both of the foregoing process involve" and should read -- Both of the foregoing processes involve --.

Column 24,
Lines 12-15 read "However, after arising technology may allow for layering methods may allow scaffolds to be...built up from...layers, stacked upon one another to form the final 3-D structure that provide an" and should read -- However, arising technology may allow for layering methods, may allow scaffolds to be...built up from...layers, stacked upon one another to form the final 3-D structure that provides an --.

Column 24,
Lines 25-26 read "such as platelet jells to increase" and should read -- such as platelet gels to increase --.

Column 24,
Lines 28-29 read "create two distinct slurries one with" and should read -- create two distinct slurries, one with --.

Column 24,
Line 64 reads "the principle concern is the" and should read -- the principal concern is the --.

Column 25,
Line 52 reads "bone graft flurry" and should read -- bone graft slurry --.

Column 26,
Line 49 reads "and tensioned on order to pull the" and should read -- and tensioned in order to pull the --.

Column 27,
Line 62 reads "slurry is prepared the as soon as possible" and should read -- slurry is prepared as soon as possible --.

Column 28,
Lines 8-9 read "to fabricate 3-D replacement graft scaffolds prior to implanting the 3-D scaffold, the stem cell molar graft" and should read -- to fabricate 3-D replacement graft scaffolds. Prior to implanting the 3-D scaffold, the stem cell molar graft --.

Column 28,
Line 66 reads "be treated in early adolescent with" and should read -- be treated in early adolescence with --.

CERTIFICATE OF CORRECTION (continued)
U.S. Pat. No. 8,470,308 B2

In the Specification:

Column 28,
Line 67 reads "Simply but, stem cell molar" and should read -- Simply put, stem cell molar --.

Column 34,
Lines 49-50 read "to include canine stems cells from" and should read -- to include canine stem cells from --.

Column 35,
Lines 8-9 read "such as collagen, ligament tendon and" and should read -- such as collagen, ligament, tendon and --.